(12) United States Patent
Moschel et al.

(10) Patent No.: US 8,188,055 B2
(45) Date of Patent: May 29, 2012

(54) INACTIVATORS OF O6-ALKYLGUANINE-DNA ALKYLTRANSFERASE

(75) Inventors: Robert C. Moschel, Frederick, MD (US); Matthew Karl Moschel, legal representative, Baltimore, MD (US); Anthony E. Pegg, Hershey, PA (US); Sahar Javanmard, Potomac, MD (US); Natalia Loktionova, Elizabeth Town, PA (US); Gary Pauly, Frederick, MD (US)

(73) Assignees: The United States of America, as represented by the Secretary, Department of Health and Human Services, Washington, DC (US); The Penn State Research Foundation, University Park, PA (US)

( * ) Notice: Subject to any disclaimer, the term of this patent is extended or adjusted under 35 U.S.C. 154(b) by 228 days.

(21) Appl. No.: 12/597,773

(22) PCT Filed: Mar. 12, 2008
(Under 37 CFR 1.47)

(86) PCT No.: PCT/US2008/056570
§ 371 (c)(1),
(2), (4) Date: Dec. 14, 2009

(87) PCT Pub. No.: WO2008/137207
PCT Pub. Date: Nov. 13, 2008

(65) Prior Publication Data
US 2010/0204172 A1    Aug. 12, 2010

Related U.S. Application Data

(60) Provisional application No. 60/915,590, filed on May 2, 2007.

(51) Int. Cl.
*A01N 43/04* (2006.01)
*A61K 31/70* (2006.01)
*C07H 17/00* (2006.01)

(52) U.S. Cl. ............... 514/43; 514/42; 514/45; 514/46; 536/27.1; 536/27.2; 536/27.21; 536/27.8

(58) Field of Classification Search .................. None
See application file for complete search history.

(56) References Cited

U.S. PATENT DOCUMENTS

| | | | |
|---|---|---|---|
| 4,235,871 A | 11/1980 | Papahadjopoulos et al. | |
| 4,501,728 A | 2/1985 | Geho et al. | |
| 4,837,028 A | 6/1989 | Allen | |
| 5,019,369 A | 5/1991 | Presant et al. | |
| 5,091,430 A | 2/1992 | Moschel et al. | |
| 5,352,669 A | 10/1994 | Moschel et al. | |
| 5,358,952 A | 10/1994 | Moschel et al. | |
| 5,525,606 A | 6/1996 | Moschel et al. | |
| 5,691,307 A | 11/1997 | Moschel et al. | |
| 5,753,668 A | 5/1998 | Moschel et al. | |
| 5,916,894 A | 6/1999 | Moschel et al. | |
| 5,958,932 A | 9/1999 | Moschel et al. | |
| 6,060,458 A | 5/2000 | Moschel et al. | |
| 6,172,070 B1 | 1/2001 | Moschel et al. | |
| 6,303,604 B1 * | 10/2001 | Moschel et al. | 514/245 |
| 6,333,331 B1 | 12/2001 | Moschel et al. | |
| 6,436,945 B2 * | 8/2002 | Moschel et al. | 514/261.1 |
| 6,528,631 B1 * | 3/2003 | Cook et al. | 536/23.1 |
| 7,825,096 B2 * | 11/2010 | Moschel et al. | 514/43 |

FOREIGN PATENT DOCUMENTS

| WO | WO 91/13898 A1 | 9/1991 |
|---|---|---|
| WO | WO 2005/068465 A1 | 7/2005 |
| WO | WO 2006/029065 A1 | 3/2006 |

OTHER PUBLICATIONS

Chae et al., *J. Med. Chem.*, 37 (3), 342-347 (1994).
Ciocco et al., *Cancer Res.*, 55, 4085-4091 (1995).
Dolan et al., *Biochem. Pharmacol.*, 46 (2), 285-290 (1993).
Dolan et al., *Proc. Natl. Acad. Sci. U.S.A.*, 87, 5368-5372 (1990).
Felker et al., *Cancer Chemother. Pharmacol.*, 32, 471-476 (1993).
Gronemeyer et al., *Protein Eng. Des. Sel.*, 19 (7), 309-316 (2006).
International Search Report PCT/US2008/056570, (2008).
Javanmard et al., *J. Med. Chem.*, 50 (21), 5193-5201 (2007).
Kokkinakis et al., *Clin. Cancer Res.*, 5, 3676-3681 (1999).
Kurpad et al., *Cancer Chemo. Pharmacol.*, 39, 307-316 (1997).
Longo, *Semin. Concol.*, 17 (6), 716-735 (1990).
Luu et al., *Biochemistry*, 41, 8689-8697 (2002).
McCormick et al., *Eur. J. Cancer*, 26 (3), 207-221 (1990).
Moschel et al., *J. Med. Chem.*, 35, 4486-4491 (1992).
Nelson et al., *J. Med. Chem.*, 47 (15), 3887-3891 (2004).

(Continued)

*Primary Examiner* — Traviss C McIntosh, III
(74) *Attorney, Agent, or Firm* — Leydig, Voit & Mayer, Ltd.

(57) ABSTRACT

Disclosed are compounds that are AGT inactivators that include a folate residue, e.g., a compound of formula (I), wherein $X^1$, $X^2$, $R^1$, and $R^2$ are as described herein. Also disclosed is a pharmaceutical composition comprising a compound of the invention and a pharmaceutically acceptable carrier. Also disclosed are methods of enhancing the chemotherapeutic treatment of tumor cells and inactivating AGT in a tumor cell. The methods comprise, inter alia, administering a compound or pharmaceutically acceptable salt of formula (I).

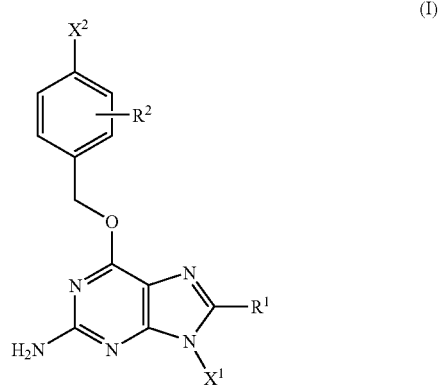

(I)

21 Claims, 5 Drawing Sheets

OTHER PUBLICATIONS

Nomura et al., *J. Org. Chem.*, 65 (16), 5016-5021 (2000).
Pegg et al., *Biochem. Pharmacol.*, 53, 1559-1564 (1997).
Pegg et al., *Prog. Nucleic Acid Res. Mol. Biol.*, 51, 167-223 (1995).
Pegg, *Cancer Research*, 50, 6119-6129 (1990).
Quinn et al., *J. Clin. Oncol.*, 20, 2277-2283 (2002).
Schold, et al., *Cancer Res.*, 56, 2076-2081 (1996).
Szoka et al., *Ann. Rev. Biophys. Bioeng.*, 9, 467 (1980).
Thomas et al., *J. Photochem. Photobiol. A: Chem.*, 135, 147-154 (2000).
Wasserman et al., *Cancer*, 36, 1258-1268 (1975).
Wei et al., *J. Med. Chem.*, 48, 256-261 (2005).

\* cited by examiner

US 8,188,055 B2

INACTIVATORS OF O6-ALKYLGUANINE-DNA ALKYLTRANSFERASE

CROSS-REFERENCE TO RELATED APPLICATIONS

This patent application claims the benefit of U.S. Provisional Patent Application No. 60/915,590, filed May 2, 2007, which is incorporated by reference.

STATEMENT REGARDING FEDERALLY SPONSORED RESEARCH AND DEVELOPMENT

This invention was made with Government support under Grant No. CA071976, awarded by the National Institutes of Health. The Government has certain rights in the invention.

BACKGROUND OF THE INVENTION $O^6$-Alkylguanine-DNA-alkyltransferase (AGT) is a DNA repair protein. AGT removes alkyl and aralkyl groups that become attached at the $O^6$-position of guanine in DNA following exposure to mutagenic and/or carcinogenic alkylating agents. It does so by bringing about a stoichiometric transfer of the group attached to the $O^6$-position of a guanine residue in DNA to a cysteine residue within the AGT protein (Pegg, Cancer Research, 50: 6119-6129 (1990)). Accordingly, AGT is beneficial to a normal cell because it removes the adducts that are formed in DNA by toxic, mutagenic and carcinogenic agents, thereby restoring the DNA to its original state and helping to prevent DNA mutations that can lead to initiation of tumor formation. Unfortunately, AGT is also beneficial to a cancerous cell because it also removes those adducts that are formed at the $O^6$-position of guanine in DNA by antineoplastic alkylating agents, such as monofunctional methylating agents, e.g., procarbazine, dacarbazine and temozolomide, and chloroethylating agents, i.e., chloroethylnitrosoureas (CENUs), such as BCNU, ACNU, CCNU, and MeCCNU (Pegg et al., Prog. Nucleic Acid Research Molec. Biol., 51: 167-223 (1995)). The resulting alkylated AGT molecule is consequently inactivated and is unable to carry out subsequent dealkylation reactions. The presence of more AGT in a cell increases its capacity to repair DNA by this mechanism compared to a cell that has less AGT.

The reduction in the efficacy of cancer chemotherapeutic drugs due to AGT, which acts without requiring the presence of additional enzymes or cofactors, and the existence of a high correlation between AGT activity and reduction in sensitivity of tumor cells to nitrosoureas have led to AGT becoming a prime target for modulation. Modulation has been attempted by two different routes. One route is indirect and involves the use of methylating agents that introduce $O^6$-methylguanine lesions into DNA for subsequent repair by AGT, thereby depleting levels of AGT. The other route is direct and involves the use of an adjuvant, i.e., an inactivator of AGT, such as an $O^6$-aralkylguanine, e.g., $O^6$-benzylguanine; see, for example, Moschel et al., U.S. Pat. Nos. 5,091,430; 5,352,669; 5,358, 952; 5,525,606; 5,691,307; 5,753,668; 5,916,894; 5,958,932; 6,060,458; 6,172,070; 6,303,604; 6,333,331; and 6,436,945. It has been shown that such adjuvants can inactivate AGT and that this inactivation can markedly improve the effectiveness of chemotherapeutic drugs that modify the $O^6$-position of DNA guanine residues (Pegg et al., Prog. Nucleic Acid Res. Mol. Biol., 51: 167-223 (1995); Kokkinakis et al., Clin. Cancer Res., 5: 3676-3681 (1999); Dolan et al., Biochem. Pharmacol., 46: 285-290 (1993); Felker et al., Cancer Chemo. Pharmacol., 32: 471-476 (1993); Schold, Jr. et al., Cancer Res., 56: 2076-2081 (1996); and Kurpad et al., Cancer Chemo. Pharmacol., 39: 307-316 (1997)). In some instances, however, in clinical trials, the adjuvant therapy produces toxic side effects in the patient (Quinn et al., J. Clin. Oncol., 2002, 20, 2277-2283). Thus, there exists a desire for compounds that are selective to the tumor cell or have reduced toxic side effects in adjuvant therapy.

BRIEF SUMMARY OF THE INVENTION

The present invention provides AGT inactivators that include a folate residue and are highly water soluble. Embodiments of the inactivator are more selective for tumor cells and toxicity to the patient is reduced.

The present invention further provides a pharmaceutical composition comprising a compound of the invention and a pharmaceutically acceptable carrier. The present invention further provides a method of enhancing the chemotherapeutic treatment of tumor cells in a mammal with an antineoplastic alkylating agent that causes cytotoxic lesions at the $O^6$-position of guanine. The method comprises administering to the mammal an effective amount of a compound of the present invention and an antineoplastic alkylating agent. The present invention also provides a method of inactivating AGT in a tumor cell comprising contacting said tumor cell with an effective amount of a compound of the invention.

While the invention has been described and disclosed below in connection with certain embodiments and procedures, it is not intended to limit the invention to those specific embodiments. Rather it is intended to cover all such alternative embodiments and modifications as fall within the spirit and scope of the invention.

BRIEF DESCRIPTION OF THE SEVERAL VIEWS OF THE DRAWING(S)

FIG. 4 depicts the release folate by cell extracts over time (h).

Figure 5:
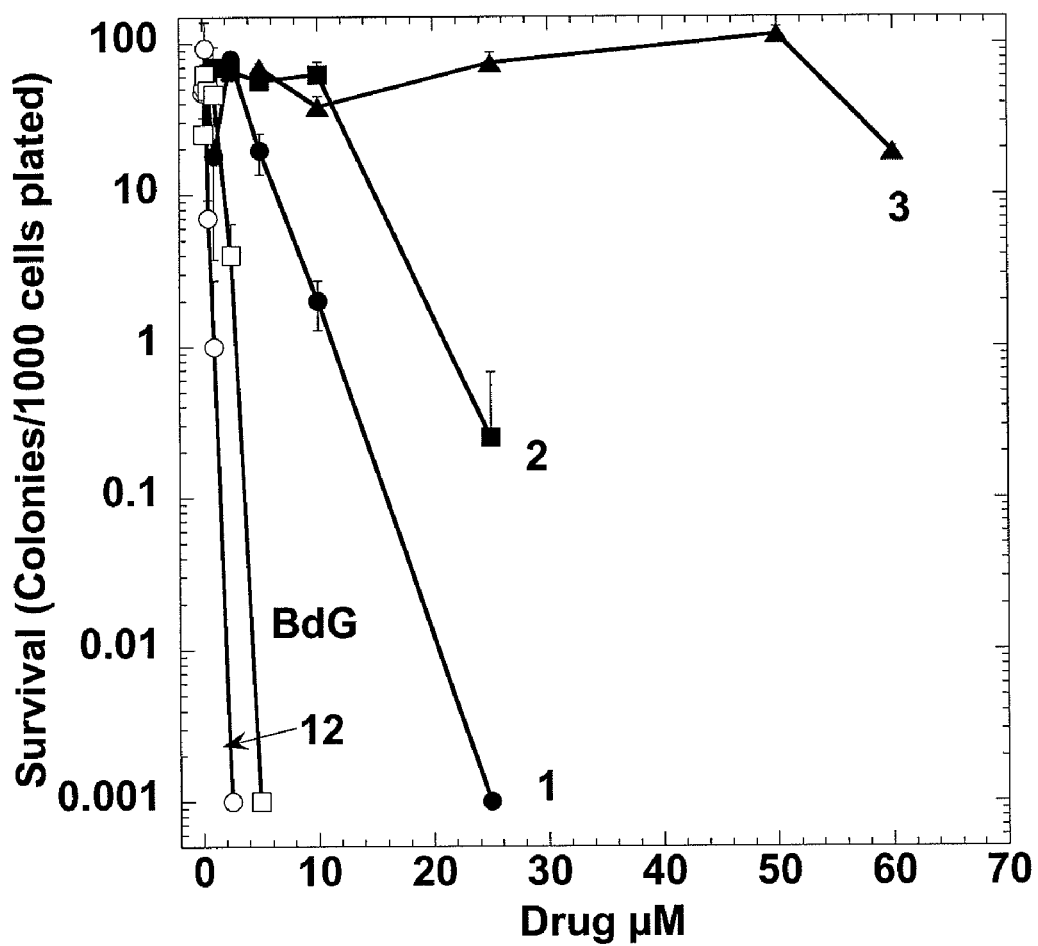

FIG. 5 depicts the killing of HT29 cells by 1,3-bis(2-chloroethyl)-1-nitrosourea (BCNU) plus alkyltransferase inhibitors. Results are shown for HT29 cells grown in RPMI medium and exposed to the drugs indicated for 2 h prior to addition of 40 μM BCNU for 2 h. Results are shown for treatment with $O^6$-benzyl-2'-deoxyguanosine (BdG) and with compounds 1, 2, 3, and 12.

Figure 6:
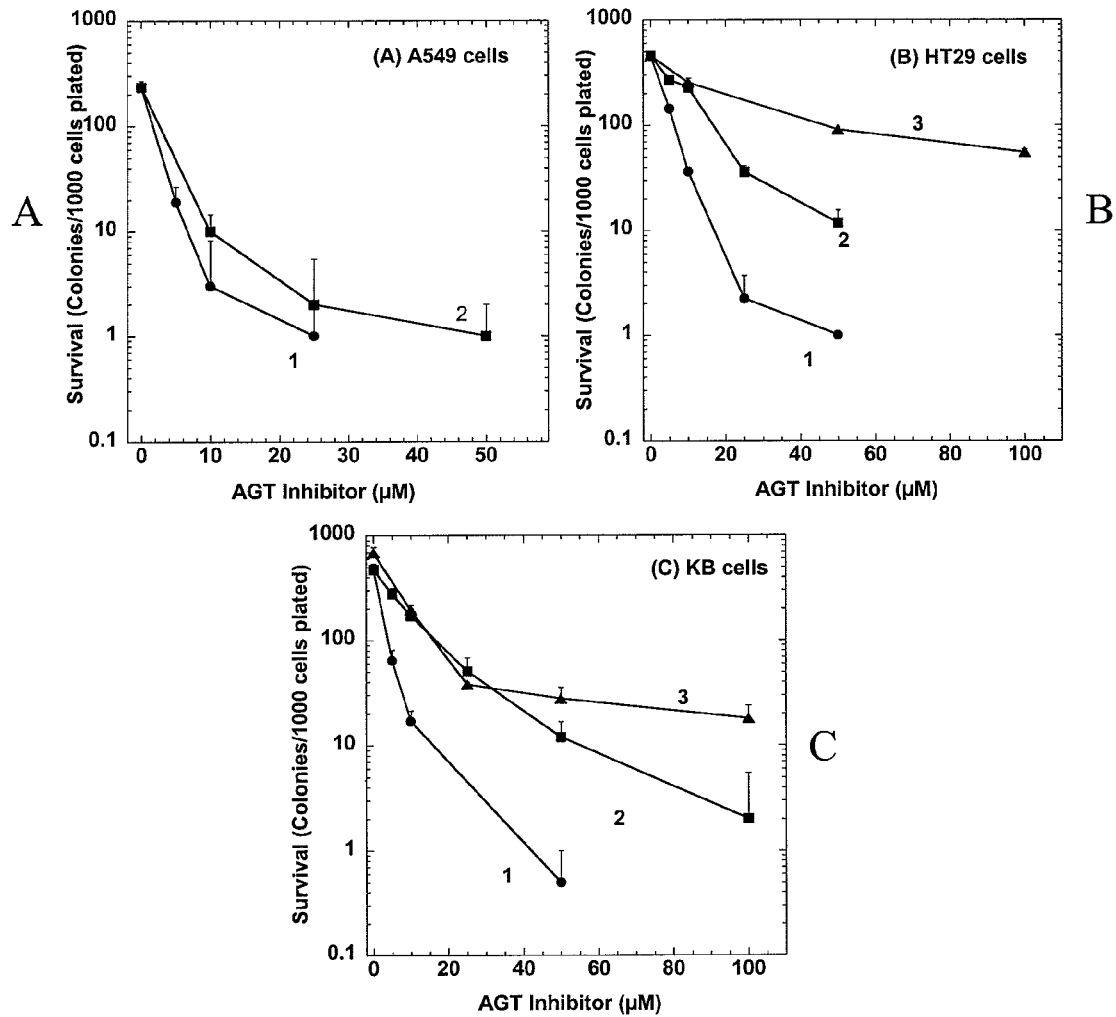

FIG. 6 depicts the killing of A549, HT29, and KB cells grown in folate-free medium by BCNU plus alkyltransferase inhibitors. Cells are grown in RPMI medium minus folate for 48 h and exposed to the drugs for 8 h prior to addition of BCNU for 2 h. FIG. 6A shows results for A549 cells treated with 1 or 2 and 20 μM BCNU. FIG. 6B shows results for HT29 cells treated with 1, 2, or 3 and 20 μM BCNU. FIG. 6C shows results for KB cells treated with 1, 2, or 3 and 40 μM BCNU.

DETAILED DESCRIPTION OF THE INVENTION

The compounds of the present invention render alkyltransferase inactivation more tumor specific. Specifically, the present inventive compounds are folate derivatives of $O^6$-benzylguanine that are selectively taken up by tumors. Thus, the present invention provides γ folate esters of $O^6$-benzyl-2'-deoxyguanosine attached through the 3' or 5' hydroxyl and folic acid γ esters of $O^6$-[4-(hydroxymethyl)benzyl]guanine of the formula (I):

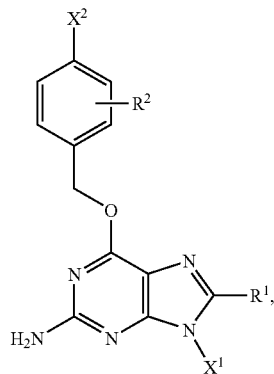

(I)

wherein
$X^1$ is selected from the group consisting of

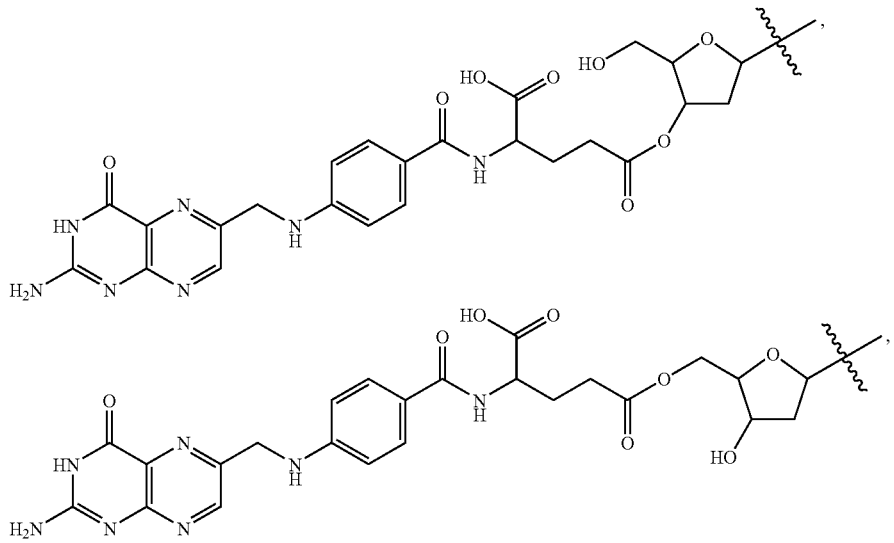

hydrogen, $C_1$-$C_6$ alkyl, $C_1$-$C_6$ aminoalkyl, $C_1$-$C_6$ hydroxyalkyl, $C_1$-$C_6$ alkylaminoalkyl, $C_1$-$C_6$ dialkylaminoalkyl, $C_1$-$C_6$ cyanoalkyl, $C_1$-$C_6$ carbamoylalkyl, $C_1$-$C_6$ pivaloylalkyl, $C_1$-$C_6$ alkylcarbonyloxy $C_1$-$C_6$ alkyl, $C_1$-$C_6$ alkoxycarbonylalkyl, ribose, 2'-deoxyribose, the conjugate acid form of a $C_1$-$C_6$ carboxyalkyl, and the carboxylate anion of a $C_1$-$C_6$ carboxyalkyl as the sodium salt;
$X^2$ is selected from the group consisting of

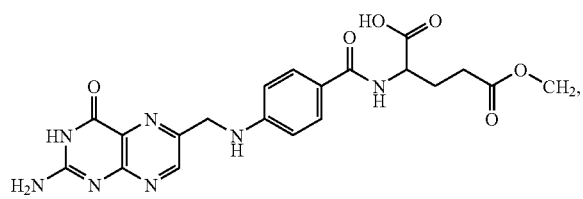

hydrogen, halo, hydroxy, a $C_1$-$C_6$ alkyl, aryl, a $C_1$-$C_6$ alkyl substituted aryl, nitro, a polycyclic aromatic $C_1$-$C_6$ alkyl containing 2-4 aromatic rings, a $C_3$-$C_8$ cycloalkyl, a $C_2$-$C_6$ alkenyl, a $C_2$-$C_6$ alkynyl, a $C_1$-$C_6$ hydroxyalkyl, a $C_1$-$C_8$ alkoxy, a $C_2$-$C_8$ alkoxyalkyl, aryloxy, acyloxy, an acyloxy-$C_1$-$C_6$ alkyl, amino, a $C_1$-$C_6$ alkylamino, a $C_1$-$C_6$ dialkylamino, acylamino, ureido, thioureido, carboxy, a carboxy-$C_1$-$C_6$ alkyl, cyano, a $C_1$-$C_6$ cyanoalkyl, C-formyl, C-acyl, a di-$C_1$-$C_6$ alkoxymethyl, an amino-$C_1$-$C_6$ alkyl, and $SO_nR^a$, wherein n is 0, 1, 2, or 3 and $R^a$ is H, a $C_1$-$C_6$ alkyl, or aryl;

$R^1$ is selected from the group consisting of hydrogen, halo, $C_1$-$C_4$ alkyl, $C_1$-$C_4$ hydroxyalkyl, mercapto, $C_1$-$C_4$ alkylthio, trifluoromethylthio, $C_1$-$C_4$ thioacyl, hydroxy, $C_1$-$C_4$ alkoxy, trifluoromethoxy, methanesulfonyloxy, trifluoromethanesulfonyloxy, $C_1$-$C_4$ acyloxy, amino, $C_1$-$C_4$ aminoalkyl, $C_1$-$C_4$ alkylamino, $C_1$-$C_4$ dialkylamino, trifluoromethylamino, ditrifluoromethylamino, aminomethanesulfonyl, $C_1$-$C_4$ aminoacyl, aminotrifluoromethylcarbonyl, formylamino, nitro, nitroso, $C_1$-$C_4$ alkyldiazo, $C_5$-$C_6$ aryldiazo, trifluoromethyl, $C_1$-$C_4$ haloalkyl, $C_1$-$C_4$ cyanoalkyl, cyano, $C_1$-$C_4$ alkyloxycarbonyl, $C_1$-$C_4$ alkylcarbonyl, phenyl, phenylcarbonyl, formyl, $C_1$-$C_4$ alkoxymethyl, phenoxymethyl, $C_2$-$C_4$ vinyl, $C_2$-$C_4$ ethynyl, and $SO_mR^b$, wherein m is 0, 1, 2, or 3 and $R^b$ is hydrogen, $C_1$-$C_4$ alkyl, amino, or aryl;

$R^2$ is selected from the group consisting of hydrogen, halo, hydroxy, a $C_1$-$C_6$ alkyl, aryl, a $C_1$-$C_6$ alkyl substituted aryl, nitro, a polycyclic aromatic $C_1$-$C_6$ alkyl containing 2-4 aromatic rings, a $C_3$-$C_8$ cycloalkyl, a $C_2$-$C_6$ alkenyl, a $C_2$-$C_6$ alkynyl, a $C_1$-$C_6$ hydroxyalkyl, a $C_1$-$C_8$ alkoxy, a $C_2$-$C_8$ alkoxyalkyl, aryloxy, acyloxy, an acyloxy-$C_1$-$C_6$ alkyl, amino, a $C_1$-$C_6$ alkylamino, a $C_1$-$C_6$ dialkylamino, acylamino, ureido, thioureido, carboxy, a carboxy-$C_1$-$C_6$ alkyl, cyano, a $C_1$-$C_6$ cyanoalkyl, C-formyl, C-acyl, a di-$C_1$-$C_6$ alkoxymethyl, an amino-$C_1$-$C_6$ alkyl, and $SO_pR^c$, wherein p is 0, 1, 2, or 3 and $R^c$ is H, a $C_1$-$C_6$ alkyl, or aryl;

provided that at least one of $X^1$ and $X^2$ is a folate residue and the other of $X^1$ and $X^2$ is a moiety other than a folate residue.

In an embodiment of the invention, the compound or pharmaceutically acceptable salt of formula (I) is a compound of formula (Ia), wherein $X^1$ is selected from the group consisting of

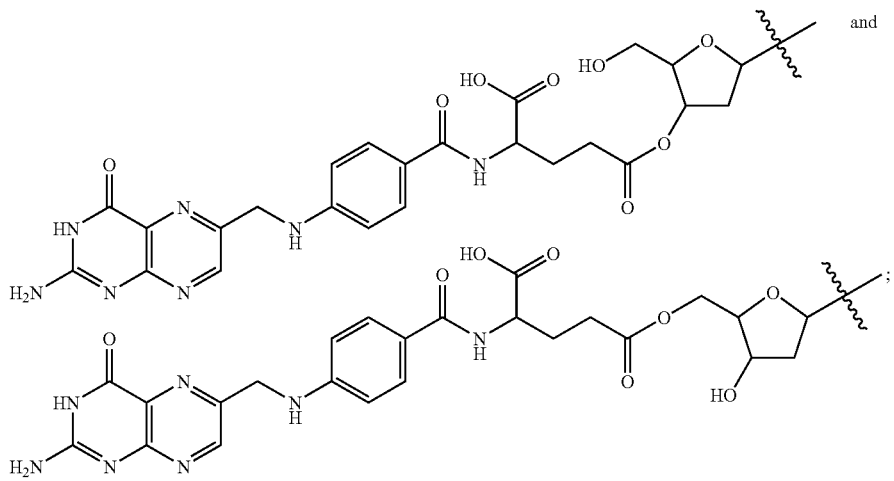

$X^2$ is selected from the group consisting of hydrogen, halo, hydroxy, a $C_1$-$C_6$ alkyl, aryl, a $C_1$-$C_6$ alkyl substituted aryl, nitro, a polycyclic aromatic $C_1$-$C_6$ alkyl containing 2-4 aromatic rings, a $C_3$-$C_8$ cycloalkyl, a $C_2$-$C_6$ alkenyl, a $C_2$-$C_6$ alkynyl, a $C_1$-$C_6$ hydroxyalkyl, a $C_1$-$C_8$ alkoxy, a $C_2$-$C_8$ alkoxyalkyl, aryloxy, acyloxy, an acyloxy-$C_1$-$C_6$ alkyl, amino, a $C_1$-$C_6$ alkylamino, a $C_1$-$C_6$ dialkylamino, acylamino, ureido, thioureido, carboxy, a carboxy-$C_1$-$C_6$ alkyl, cyano, a $C_1$-$C_6$ cyanoalkyl, C-formyl, C-acyl, a di-$C_1$-$C_6$ alkoxymethyl, an amino-$C_1$-$C_6$ alkyl, and $SO_nR^a$, wherein n is 0, 1, 2, or 3 and $R^a$ is H, a $C_1$-$C_6$ alkyl, or aryl;

$R^1$ is selected from the group consisting of hydrogen, halo, $C_1$-$C_4$ alkyl, $C_1$-$C_4$ hydroxyalkyl, mercapto, $C_1$-$C_4$ alkylthio, trifluoromethylthio, thioacyl, hydroxy, $C_1$-$C_4$ alkoxy, trifluoromethoxy, methanesulfonyloxy, trifluoromethanesulfonyloxy, $C_1$-$C_4$ acyloxy, amino, $C_1$-$C_4$ aminoalkyl, $C_1$-$C_4$ alkylamino, $C_1$-$C_4$ dialkylamino, trifluoromethylamino, ditrifluoromethylamino, aminomethanesulfonyl, $C_1$-$C_4$ aminoacyl, aminotrifluoromethylcarbonyl, formylamino, nitro, nitroso, $C_1$-$C_4$ alkyldiazo, $C_5$-$C_6$ aryldiazo, trifluoromethyl, $C_1$-$C_4$ haloalkyl, $C_1$-$C_4$ cyanoalkyl, cyano, $C_1$-$C_4$ alkyloxycarbonyl, $C_1$-$C_4$ alkylcarbonyl, phenyl, phenylcarbonyl, formyl, $C_1$-$C_4$ alkoxymethyl, phenoxymethyl, $C_2$-$C_4$ vinyl, $C_2$-$C_4$ ethynyl, and $SO_mR^b$, wherein m is 0, 1, 2, or 3 and $R^b$ is hydrogen, $C_1$-$C_4$ alkyl, amino, or aryl;

$R^2$ is selected from the group consisting of hydrogen, halo, hydroxy, a $C_1$-$C_6$ alkyl, aryl, a $C_1$-$C_6$ alkyl substituted aryl, nitro, a polycyclic aromatic $C_1$-$C_6$ alkyl containing 2-4 aromatic rings, a $C_3$-$C_8$ cycloalkyl, a $C_2$-$C_6$ alkenyl, a $C_2$-$C_6$ alkynyl, a $C_1$-$C_6$ hydroxyalkyl, a $C_1$-$C_8$ alkoxy, a $C_2$-$C_8$ alkoxyalkyl, aryloxy, acyloxy, an acyloxy-$C_1$-$C_6$ alkyl, amino, a $C_1$-$C_6$ alkylamino, a $C_1$-$C_6$ dialkylamino, acylamino, ureido, thioureido, carboxy, a carboxy-$C_1$-$C_6$ alkyl, cyano, a $C_1$-$C_6$ cyanoalkyl, formyl, acyl, a di-$C_1$-$C_6$ alkoxymethyl, a $C_1$-$C_6$ aminoalkyl, and $SO_pR^c$, wherein p is 0, 1, 2, or 3 and $R^c$ is H, a $C_1$-$C_6$ alkyl, or aryl.

In the compound of formula (Ia), $R^1$ preferably is hydrogen, halo, $C_1$-$C_4$ alkyl, $C_1$-$C_4$ hydroxyalkyl, mercapto, $C_1$-$C_4$ alkylthio, hydroxy, $C_1$-$C_4$ alkoxy, amino, $C_1$-$C_4$ aminoalkyl, $C_1$-$C_4$ alkylamino, $C_1$-$C_4$ dialkylamino, nitro, $C_1$-$C_4$ haloalkyl, $C_1$-$C_4$ cyanoalkyl, cyano, phenyl, phenylcarbonyl, or $C_1$-$C_4$ alkoxymethyl. Also in a compound of formula (Ia), $X^2$ and $R^2$ are the same or different and each preferably is hydrogen, halo, hydroxy, a $C_1$-$C_6$ alkyl, aryl, nitro, a $C_1$-$C_6$ hydroxyalkyl, a $C_1$-$C_8$ alkoxy, a aryloxy, amino, a $C_1$-$C_6$ alkylamino, a $C_1$-$C_6$ dialkylamino, carboxy, a carboxy-$C_1$-$C_6$ alkyl, cyano, a $C_1$-$C_6$ cyanoalkyl, or a $C_1$-$C_6$ aminoalkyl. Preferably $X^2$ and $R^2$ are both hydrogen.

Preferred compounds of formula (I) are the compounds or salts of formula (Ia):

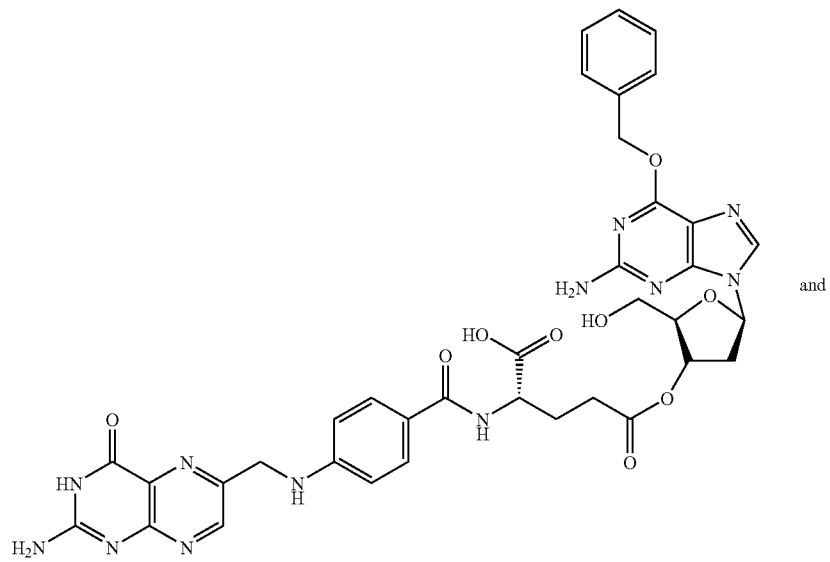

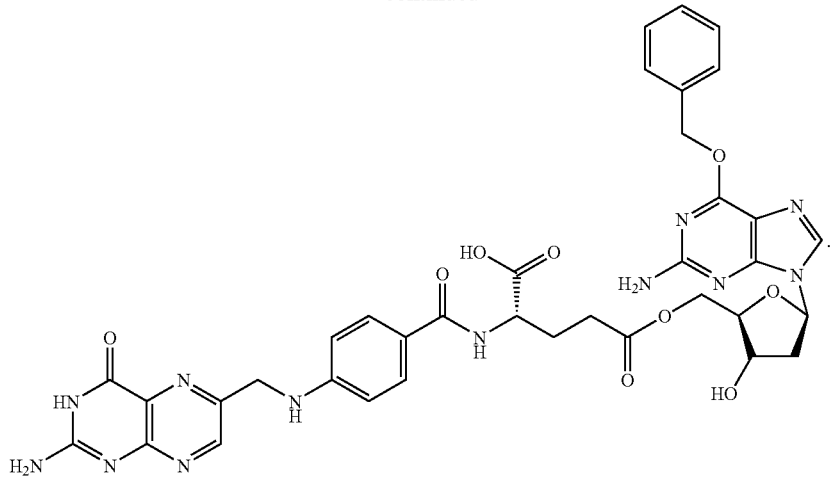

In another embodiment of the present invention, the compound or pharmaceutically acceptable salt of formula (I) includes a compound or salt of formula (Ib), wherein $X^1$ is selected from the group consisting of hydrogen, $C_1$-$C_6$ alkyl, $C_1$-$C_6$ aminoalkyl, $C_1$-$C_6$ hydroxyalkyl, $C_1$-$C_6$ alkylaminoalkyl, $C_1$-$C_6$ dialkylaminoalkyl, $C_1$-$C_6$ cyanoalkyl, $C_1$-$C_6$ carbamoylalkyl, $C_1$-$C_6$ pivaloylalkyl, $C_1$-$C_6$ alkylcarbonyloxy $C_1$-$C_6$ alkyl, $C_1$-$C_6$ alkoxycarbonylalkyl, ribose, 2'-deoxyribose, the conjugate acid form of a $C_1$-$C_6$ carboxyalkyl, and the carboxylate anion of a $C_1$-$C_6$ carboxyalkyl as the sodium salt;

$X^2$ is

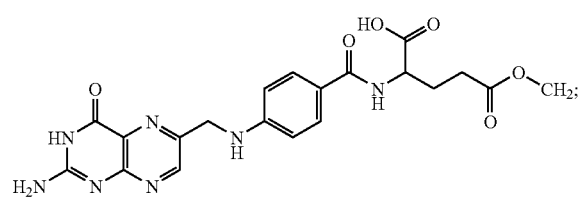

$R^1$ is selected from the group consisting of hydrogen, halo, $C_1$-$C_4$ alkyl, $C_1$-$C_4$ hydroxyalkyl, mercapto, $C_1$-$C_4$ alkylthio, trifluoromethylthio, $C_1$-$C_4$ thioacyl, hydroxy, $C_1$-$C_4$ alkoxy, trifluoromethoxy, methanesulfonyloxy, trifluoromethanesulfonyloxy, $C_1$-$C_4$ acyloxy, amino, $C_1$-$C_4$ aminoalkyl, $C_1$-$C_4$ alkylamino, $C_1$-$C_4$ dialkylamino, trifluoromethylamino, ditrifluoromethylamino, aminomethanesulfonyl, $C_1$-$C_4$ aminoacyl, aminotrifluoromethylcarbonyl, formylamino, nitro, nitroso, $C_1$-$C_4$ alkyldiazo, $C_5$-$C_6$ aryldiazo, trifluoromethyl, $C_1$-$C_4$ haloalkyl, $C_1$-$C_4$ cyanoalkyl, cyano, alkyloxycarbonyl, $C_1$-$C_4$ alkylcarbonyl, phenyl, phenylcarbonyl, formyl, alkoxymethyl, phenoxymethyl, $C_2$-$C_4$ vinyl, $C_2$-$C_4$ ethynyl, and $SO_mR^b$, wherein m is 0, 1, 2, or 3 and $R^b$ is hydrogen, $C_1$-$C_4$ alkyl, amino, or phenyl;

$R^2$ is selected from the group consisting of hydrogen, halo, hydroxy, a $C_1$-$C_6$ alkyl, aryl, a $C_1$-$C_6$ alkyl substituted aryl, nitro, a polycyclic aromatic $C_1$-$C_6$ alkyl containing 2-4 aromatic rings, a $C_3$-$C_8$ cycloalkyl, a $C_2$-$C_6$ alkenyl, a $C_2$-$C_6$ alkynyl, a $C_1$-$C_6$ hydroxyalkyl, a $C_1$-$C_8$ alkoxy, a $C_2$-$C_8$ alkoxyalkyl, aryloxy, acyloxy, an acyloxy-$C_1$-$C_6$ alkyl, amino, a $C_1$-$C_6$ alkylamino, a $C_1$-$C_6$ dialkylamino, acylamino, ureido, thioureido, carboxy, a carboxy-$C_1$-$C_6$ alkyl, cyano, a $C_1$-$C_6$ cyanoalkyl, formyl, acyl, a di-$C_1$-$C_6$ alkoxymethyl, an $C_1$-$C_6$ aminoalkyl, and $SO_pR^c$, wherein p is 0, 1, 2, or 3 and $R^c$ is H, a $C_1$-$C_6$ alkyl, or aryl.

In the compound of formula (Ib), $R^1$ preferably is hydrogen, halo, $C_1$-$C_4$ alkyl, $C_1$-$C_4$ hydroxyalkyl, mercapto, $C_1$-$C_4$ alkylthio, hydroxy, $C_1$-$C_4$ alkoxy, amino, $C_1$-$C_4$ aminoalkyl, $C_1$-$C_4$ alkylamino, $C_1$-$C_4$ dialkylamino, nitro, $C_1$-$C_4$ haloalkyl, $C_1$-$C_4$ cyanoalkyl, cyano, phenyl, phenylcarbonyl, or $C_1$-$C_4$ alkoxymethyl. Also in a compound of formula (Ib), $R^2$ preferably is hydrogen, halo, hydroxy, a $C_1$-$C_6$ alkyl, aryl, nitro, a $C_1$-$C_6$ hydroxyalkyl, a $C_1$-$C_8$ alkoxy, a aryloxy, amino, a $C_1$-$C_6$ alkylamino, a $C_1$-$C_6$ dialkylamino, carboxy, a carboxy-$C_1$-$C_6$ alkyl, cyano, a $C_1$-$C_6$ cyanoalkyl, or a $C_1$-$C_6$ aminoalkyl. In an embodiment, in the compound of formula (Ib), $X^1$ is selected from the group consisting of hydrogen, $C_1$-$C_6$ alkyl, $C_1$-$C_6$ aminoalkyl, $C_1$-$C_6$ hydroxyalkyl, $C_1$-$C_6$ alkylaminoalkyl, $C_1$-$C_6$ dialkylaminoalkyl, and $C_1$-$C_6$ cyanoalkyl. Preferably, $X^1$ is hydrogen.

A preferred compound of formula (I) is a compound or salt of formula (Ib):

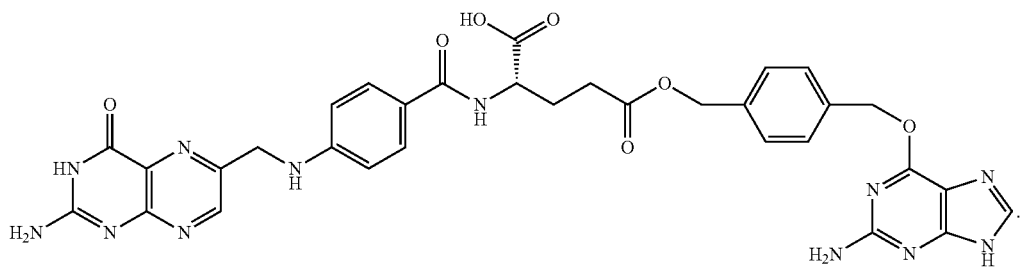

The compounds of formula (I) can be used as pharmaceutically acceptable salts. Examples of pharmaceutically acceptable salts include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, and arylsulfonic acids. An example of arylsulphonic acid is p-toluenesulphonic acid. The carboxyl group of a compound of formula (I) can be converted to salts known to those skilled in the art, for example, a salt of an alkali metal (e.g., sodium or potassium), alkaline earth metal (e.g., calcium), or ammonium salt.

The compound of formula (I) can be chiral or achiral. If the compound is chiral, it can be the R enantiomer, the S enantiomer, or a mixture of both (including a racemic mixture). If more than one chiral center is present, the stereoisomers of the compound of Formula I can be diastereomers of one another and can include a meso compound.

The compounds of formula (I) are advantageous as they have or are expected to have increased solubility in water as they can become negatively charged upon solvation. For example, some compounds of formula (I) are 20 or more times, preferably 100 or more times, specifically hundred or more times, e.g., 700 to 1000 times or more, soluble in water than $O^6$-benzylguanine. Accordingly, the compounds of the present invention can be administered in simple aqueous formulations that require little or no organic diluents. The compounds are, therefore, extremely useful for intratumoral administration.

Figure 1:
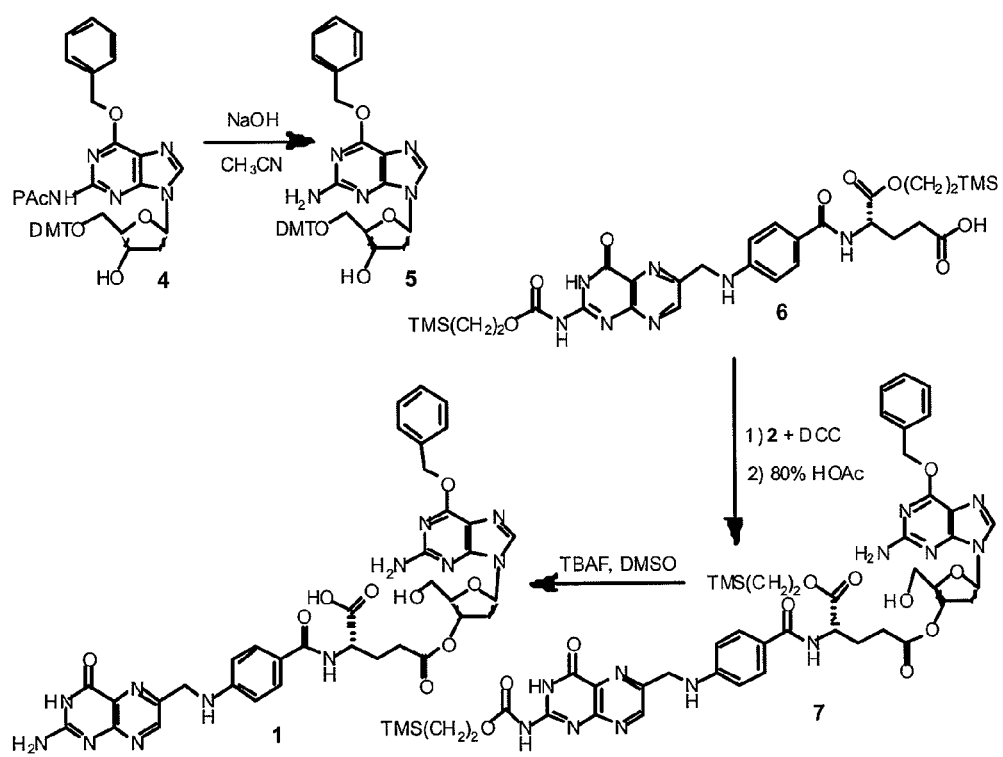
FIG. 1 depicts a reaction scheme to prepare compound 1 in accordance with an embodiment of the invention.
Figure 2:
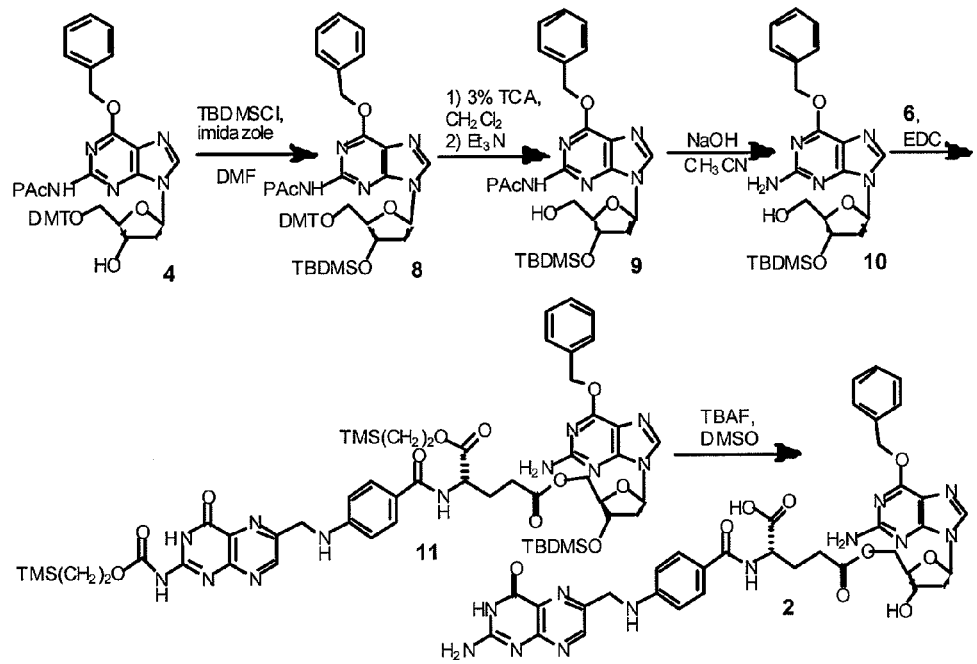
FIG. 2 depicts a reaction scheme to prepare compound 2 in accordance with an embodiment of the invention.
Figure 3:
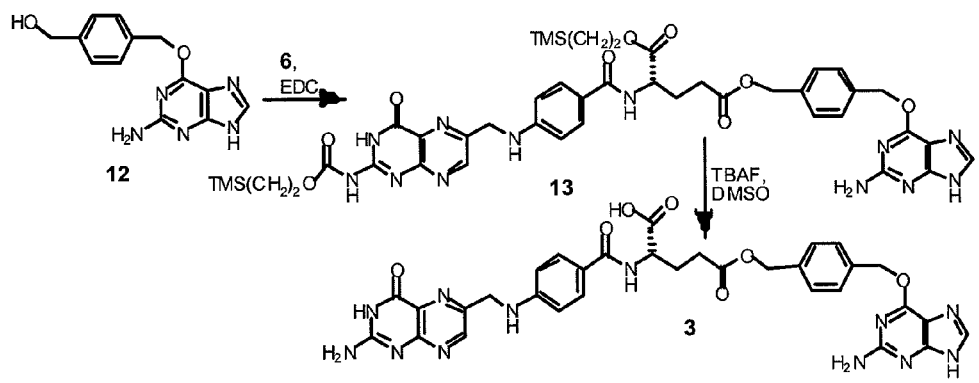
FIG. 3 depicts a reaction scheme to prepare compound 3 in accordance with an embodiment of the invention.

Compounds of formula (I) can be prepared by any suitable method. For example, a compound of formula (Ia), the 3' and 5' γ folate esters of $O^6$-benzyldeoxyguanosine, can be prepared from $O^6$-benzyl-5'-O-(4,4'-dimethoxytrityl)-$N^2$-phenoxyacetyl-2'-deoxyguanosine (4) (FIGS. 1 and 2). Compound 4 has been previously prepared for use in the synthesis of oligonucleotides containing $O^6$-benzyldeoxyguanosines (Luu et al., *Biochemistry* 2002, 41, 8689-8697). Protecting groups on the nucleoside are manipulated to give $O^6$-benzyldeoxyguanosine having either a free 3' hydroxyl (FIG. 1) or free 5' hydroxyl (FIG. 2) which can be selectively coupled to the γ carboxylate of bis-silyl protected folic acid (Nomura et al., *J. Org. Chem.* 2000, 11, 5016-5021) using a carbodiimide. To prepare a compound of formula (Ib), the γ folate ester of $O^6$-[4-(hydroxymethyl)benzyl]guanine (12) can be prepared similarly by carbodiimide coupling of the hydroxyl group on the $O^6$-modified guanine (12) which can be prepared as described (Chae et al., *J. Med. Chem.* 1994, 37, 342-347) to the same silyl protected folate. The resulting esters can be, for example, purified, deprotected, and subsequently isolated by mild acid precipitation (FIG. 3).

The present invention further provides a pharmaceutical composition comprising a compound of formula (I), which includes compounds of formula (Ia) and (Ib), and a pharmaceutically acceptable carrier.

Generally, the compound of formula (I) will be administered in a pharmaceutical composition to an individual afflicted with a cancer. Those undergoing or about to undergo chemotherapy can be treated with at least one compound of formula (I) separately or in conjunction with other treatments, as appropriate. In therapeutic applications, compositions are administered to a patient in an amount sufficient to elicit an effective depression of AGT activity thereby potentiating the cytotoxicity of the chemotherapeutic treatment. An amount adequate to accomplish this is defined as a "therapeutically effective dose," which is also an "AGT inactivating effective amount." Amounts effective for a therapeutic or prophylactic use will depend on, e.g., the stage and severity of the disease being treated, the age, weight, and general state of health of the patient, and the judgment of the prescribing physician. The size of the dose will also be determined by the compound of formula (I) selected, method of administration, timing and frequency of administration as well as the existence, nature, and extent of any adverse side-effects that might accompany the administration of a particular compound of formula (I) and the desired physiological effect. It will be appreciated by one of skill in the art that various disease states may require prolonged treatment involving multiple administrations, perhaps using a series of different prodrugs of AGT inactivators and/or chemotherapeutic agents in each or various rounds of administration.

Suitable chemotherapeutic agents administered in coordination with at least one compound of formula (I) of the present invention include alkylating agents, such as chloroethylating and methylating agents. Such agents can be administered using techniques such as those described in, for example, Wasserman et al., *Cancer*, 36, pp. 1258-1268 (1975) and *Physicians' Desk Reference*, 58th ed., Thomson PDR (2004). For example, 1,3-bis(2-chloroethyl)-1-nitrosourea (carmustine or BCNU, Bristol-Myers, Evansville, Ind.) can be administered intravenously at a dosage of about 40 mg/m$^2$ when $O^6$-benzylguanine is employed. Other alkylating agents can be administered in appropriate dosages via routes of administration known to skilled medical practitioners.

Suitable doses and dosage regimens can be determined by conventional range-finding techniques known to those of ordinary skill in the art. Generally, treatment is initiated with smaller dosages that are less than the optimum dose of the compound of formula (I). Thereafter, the dosage is increased by small increments until the optimum effect under the circumstances is reached. The present inventive method can involve the administration of about 0.1 μg to about 50 mg of at least one compound of formula (I) per kg body weight of the individual. For a 70 kg patient, dosages of from about 10 μg to about 200 mg of the compound of formula (I) would be more commonly used, depending on a patient's physiological response, as determined by measuring cancer-specific antigens or other measurable parameters related to the tumor load of a patient.

The compound of formula (I) and compositions of the present invention can be employed in many disease states including life-threatening or potentially life-threatening situations. In view of the relatively less toxic nature of the compound of formula (I), it is possible and can be desirable by the treating physician to administer some or substantial excess of the compound of formula (I). Single or multiple administrations of the compound of formula (I) can be carried out with dose levels and pattern being selected by the treating physician. In any event, the pharmaceutical formulations should provide a quantity of AGT-inactivating compound of formula (I) sufficient to effectively enhance the cytotoxic impact of the chemotherapy.

The pharmaceutical compositions for therapeutic treatment are intended for parenteral, topical, oral or local administration and generally comprise a pharmaceutically acceptable carrier and an amount of the active ingredient sufficient to reduce, and preferably prevent, the activity of the AGT protein. The carrier can be any of those conventionally used and is limited only by chemico-physical considerations, such as solubility and lack of reactivity with the compound of formula (I), and by the route of administration.

The pharmaceutically acceptable carrier (or excipient) is preferably one that is chemically inert to the compound of formula (I) and one that has no detrimental side effects or toxicity under the conditions of use. Such pharmaceutically acceptable carriers preferably include saline (e.g., 0.9% saline), Cremophor EL (which is a derivative of castor oil and ethylene oxide available from Sigma Chemical Co., St. Louis, Mo.) (e.g., 5% Cremophor EL/5% ethanol/90% saline, 10% Cremophor EL/90% saline, or 50% Cremophor EL/50% ethanol), propylene glycol (e.g., 40% propylene glycol/10% ethanol/50% water), polyethylene glycol (e.g., 40% PEG400/ 60% saline), and alcohol (e.g., 40% ethanol/60% water). A preferred pharmaceutical carrier is polyethylene glycol, such as PEG 400, and particularly a composition comprising 40% PEG 400 and 60% water or saline. The choice of carrier will be determined in part by the particular compound chosen, as well as by the particular method used to administer the composition. Accordingly, there is a wide variety of suitable formulations of the pharmaceutical composition of the present invention.

The following formulations for oral, aerosol, parenteral, subcutaneous, intravenous, intraarterial, intramuscular, interperitoneal, rectal, and vaginal administration are merely exemplary and are in no way limiting. The pharmaceutical compositions can be administered parenterally, e.g., intravenously, intraarterially, subcutaneously, intradermally, or intramuscularly. Thus, the invention provides compositions for parenteral administration that comprise a solution of the compound of formula (I) dissolved or suspended in an acceptable carrier suitable for parenteral administration, including aqueous and non-aqueous, isotonic sterile injection solutions.

Overall, the requirements for effective pharmaceutical carriers for parenteral compositions are well known to those of ordinary skill in the art. See *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Toissel, 4th ed., pages 622-630 (1986). Such compositions include solutions containing anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound of formula (I) can be administered in a physiologically acceptable diluent in a pharmaceutical carrier, such as a sterile liquid or mixture of liquids, including water, saline, aqueous dextrose and related sugar solutions, an alcohol, such as ethanol, isopropanol (for example in topical applications), or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils useful in parenteral formulations include petroleum, animal, vegetable, and synthetic oils. Specific examples of oils useful in such formulations include peanut, soybean, sesame, cottonseed, corn, olive, petrolatum, and mineral oil. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl-β-aminopropionates, and 2-alkyl-imidazoline quaternary ammonium salts, and (e) mixtures thereof.

The parenteral formulations typically will contain from about 0.5% or less to about 25% or more by weight of the compound of formula (I) in solution. Preservatives and buffers can be used. In order to minimize or eliminate irritation at the site of injection, such compositions can contain one or more nonionic surfactants having a hydrophile-lipophile balance (HLB) of from about 12 to about 17. The quantity of surfactant in such formulations will typically range from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Topical formulations, including those that are useful for transdermal drug release, are well known to those of skill in the art and are suitable in the context of the present invention for application to skin.

Formulations suitable for oral administration can consist of (a) liquid solutions, such as an effective amount of the compound of formula (I) dissolved in diluents, such as water, saline, or orange juice; (b) capsules, sachets, tablets, lozenges, and troches, each containing a pre-determined amount of the compound of formula (I), as solids or granules; (c) powders; (d) suspensions in an appropriate liquid; and (e) suitable emulsions. Liquid formulations can include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising a compound of formula (I) in an inert base, such as gelatin and glycerin, or sucrose and acacia, emulsions, gels, and the like containing, in addition to the compound of formula (I), such excipients as are known in the art.

The compound of formula (I) of the present invention, alone or in combination with other suitable components, can be made into aerosol formulations to be administered via inhalation. The at least one compound of formula (I) is preferably supplied in finely divided form along with a surfactant and propellant. Typical percentages of the compound of formula (I) can be about 0.01% to about 20% by weight, preferably about 1% to about 10% by weight. The surfactant must, of course, be nontoxic, and preferably soluble in the propellant. Representative of such surfactants are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides can be employed. The surfactant can constitute from about 0.1% to about 20% by weight of the composition, preferably from about 0.25% to about 5%. The balance of the composition is ordinarily propellant. A carrier can also be included as desired, e.g., lecithin, for intranasal delivery. These aerosol formulations can be placed into acceptable pressurized propellants, such as dichlorodifluoromethane, propane, nitrogen, and the like. They also can be formulated as pharmaceuticals for non-pressured preparations, such as in a nebulizer or an atomizer. Such spray formulations can be used to spray mucosa.

Additionally, the compound of formula (I) can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

The concentration of the inactivators or prodrugs of the present invention in the pharmaceutical formulations can vary, e.g., from less than about 1%, usually at or at least about 10%, to as much as 20% to 50% or more by weight, and can be selected primarily by fluid volumes, and viscosities, in accordance with the particular mode of administration selected.

Thus, a typical pharmaceutical composition for intravenous infusion could be made up to contain 250 ml of sterile Ringer's solution, and 100 mg of at least one compound of formula (I). Actual methods for preparing parenterally administrable compounds of formula (I) will be known or apparent to those skilled in the art and are described in more detail in, for example, *Remington's Pharmaceutical Science* (17th ed., Mack Publishing Company, Easton, Pa., 1985).

It will be appreciated by one of ordinary skill in the art that, in addition to the aforedescribed pharmaceutical compositions, the compound of formula (I) can be formulated as inclusion complexes, such as cyclodextrin inclusion complexes, or liposomes. Liposomes can serve to target the compound of formula (I) to a particular tissue, such as lymphoid tissue or cancerous hepatic cells. Liposomes can also be used to increase the half-life of the compound of formula (I). Many methods are available for preparing liposomes, as described in, for example, Szoka et al., *Ann. Rev. Biophys. Bioeng.*, 9, 467 (1980) and U.S. Pat. Nos. 4,235,871, 4,501,728, 4,837,028, and 5,019,369.

The present invention has applicability to the treatment of any type of cancer capable of being treated with an antineoplastic alkylating agent which causes cytotoxic lesions at the $O^6$-position of guanine. Such cancers include, for example, colon tumors, prostate tumors, brain tumors, lymphomas, leukemias, breast tumors, ovarian tumors, lung tumors, Wilms' tumor, rhabdomyosarcoma, multiple myeloma, stomach tumors, soft-tissue sarcomas, Hodgkin's disease, and non-Hodgkin's lymphomas.

The present invention further provides a method of enhancing the chemotherapeutic treatment of tumor cells in a mammal with an antineoplastic alkylating agent that causes cytotoxic lesions at the $O^6$-position of guanine, which method comprises administering to a mammal an effective amount of at least one compound of formula (I) and administering to said mammal an effective amount of an antineoplastic alkylating agent which causes cytotoxic lesions at the $O^6$-position of guanine.

The present invention also provides a method of enhancing the effect of an antineoplastic alkylating agent, which alkylates the $O^6$-position of guanine residues in DNA, in the chemotherapeutic treatment of cancer in a mammal, particularly a human. The method comprises co-administering to the mammal a cancer-treatment effective amount of an antineoplastic alkylating agent and a chemotherapeutic treatment-enhancing amount of at least one compound of formula (I) in accordance with the present invention. By "enhancing the effect of an antineoplastic alkylating agent" is meant that the antineoplastic alkylating agent has a greater effect in the presence of at least one compound of formula (I) of the present invention than in the absence of the compound of formula (I). When an alkyltransferase acts on the compound of formula (I), it is inactivated and, therefore, is not able to act on the DNA in a cancerous cell that has been alkylated by the antineoplastic alkylating agent. Given that the alkyltransferase is not able to act on the alkylated DNA in a cancerous cell, the DNA in the cancerous cell is not repaired, thereby leading to death of the cancerous cell.

By "coadministering" is meant administering the antineoplastic alkylating agent and the compound of formula (I) sufficiently close in time such that the compound of formula (I) can enhance the effect of the antineoplastic alkylating agent. In this regard, the compound of formula (I) can be administered first and the antineoplastic alkylating agent can be administered second, or vice versa. Alternatively, the compound of formula (I) and the antineoplastic alkylating agent can be administered simultaneously. In addition, a combination of compounds of formula (I) can be administered, and one or more of the compounds of formula (I) can be administered in combination with another agent useful in the treatment of cancer.

The antineoplastic alkylating agent is administered in a dose sufficient to treat the cancer (e.g., cancer-treatment effective amount of an antineoplastic alkylating agent). Such doses are known in the art (see, for example, the *Physicians' Desk Reference* (2004)). For example, 1,3-bis(2-chloroethyl)-1-nitrosourea (carmustine or BCNU, Bristol-Myers, Evansville, Ind.) can be administered intravenously to a patient at a dosage of from about 150 to 200 mg/m$^2$ every six weeks. Another alkylating agent, namely 1-(2-chloroethyl)-3-cyclohexyl-1-nitrosourea (lomustine or CCNU, Bristol-Myers), can be administered orally at a dosage of about 130 mg/m$^2$ every six weeks.

The compound of formula (I) is administered in a dose sufficient to enhance the effect of the antineoplastic alkylating agent (e.g., a chemotherapeutic treatment-enhancing amount). A suitable dosage is that which will result in a concentration of the compound of formula (I) in the cancerous cells to be treated sufficient to deplete alkyltransferase activity, e.g., from about 10 nM to 200 nM intracellularly, which can require an extracellular concentration of from about 10 µM to 50 µM. The dose can be adjusted as necessary to enhance the effect of the antineoplastic alkylating agent.

The compounds of formula (I) of the present invention are useful in enhancing the effect of any suitable antineoplastic alkylating agent that alkylates the $O^6$-position of guanine residues in DNA. Examples of antineoplastic alkylating agents include chloroethylating agents. The most frequently used chloroethylating agents include 1-(2-chloroethyl)-3-cyclohexyl-1-nitrosourea (CCNU, lomustine), 1,3-bis(2-chloroethyl)-1-nitrosourea (BCNU, carmustine), 1-(2-chloroethyl)-3-(4-methylcyclohexyl)-1-nitrosourea (MeCCNU, semustine), and 1-(2-chloroethyl)-3-(4-amino-2-methyl-5-pyrimidinyl)methyl-1-nitrosourea (ACNU). Such agents have been used clinically against tumors of the central nervous system, multiple myeloma, melanoma, lymphoma, gastrointestinal tumors, and other solid tumors (Colvin and Chabner. Alkylating Agents. In: Cancer Chemotherapy: Principles and Practice. Edited by B. A. Chabner and J. M. Collins, Lippincott, Philadelphia, Pa. pp. 276-313 (1990); and McCormick et al., *Eur. J. Cancer* 26: 207-221 (1990)). Chloroethylating agents, which have fewer side effects and are currently under development include 1-(2-chloroethyl)-3-(2-hydroxyethyl)-1-nitrosourea (HECNU), 2-chloroethylmethylsulfonylmethanesulfonate (Clomesone), and 1-[N-(2-chloroethyl)-N-nitrosoureido]ethylphosphonic acid diethyl ester (Fotemustine) (Colvin and Chabner (1990), supra; and McCormick et al. (1990), supra). Methylating agents include Streptozotocin (2-deoxy-2-(3-methyl-3-nitrosoureido)-D-glucopyranose), Procarbazine (N-(1-methylethyl)-4-[(2-methylhydrazino)methyl]benzamide), Dacarbazine or DTIC (5-(3,3-dimethyl-1-triazenyl)-1H-imidazole-4-carboxamide), and Temozolomide (8-carbamoyl-3-methylimidazo[5.1-d]-1,2,3,5-tetrazin-4-(3H)-one).

Temozolomide is active against malignant melanomas, brain tumors, and mycosis fungoides. Streptozotocin is effective against pancreatic tumors. Procarbazine is used to treat Hodgkin's disease and brain tumors. DTIC is used to treat melanoma and lymphomas (Colvin and Chabner (1990), supra; and Longo, *Semin. Concol.*, 17: 716-735 (1990)).

The antineoplastic alkylating agent can be administered by any route. Conventional means of administration are described in Wasserman et al. (*Cancer*, 36: 1258-1268 (1975)) and in *Physicians' Desk Reference* (2004).

The following examples further illustrate the invention but, of course, should not be construed as in any way limiting its scope.

Chemicals can be obtained from Aldrich (Milwaukee, Wis.) or Sigma (St. Louis, Mo.) and are used without further purification. UV spectra are determined on a Beckman Coulter DU 7400 spectrophotometer. $^1$H NMR spectra are recorded in DMSO-$d_6$ with a Varian INOVA 400 MHz spectrometer. Chemical shifts are reported as δ values in parts per million relative to TMS as an internal standard. Splitting pattern abbreviations are as follows: s=singlet, d=doublet, dd=double doublet, ddd=a doublet of doublet of doublets, t=triplet, td=triplet of doublets, m=multiplet. Coupling constants are in hertz. Mass spectra are collected on a Thermo Finnigan TSQ Quantum spectrometer in positive ion electrospray mode scanning m/z=100 to 1500 in one second. The electrospray voltage is 3.5 kV, the transfer tube is at 350° C. Elemental analysis can be performed by Atlantic Microlab, Inc. (Norcross, Ga.) and are within 0.4% of theoretical values calculated for C, H, and N. All silica gel chromatography is carried out using Davisil, grade 633, 200-425 mesh 60 Å. Synthesis and purification of folate containing compounds is performed under reduced (yellow) light, and these materials are considered light sensitive (Thomas et al., *J. Photochem. Photobiol. A: Chem.*, 2000, 135, 147-154).

Example 1

This example demonstrates a synthesis of $O^6$-Benzyl-3'-O-[γ-folyl]-2'-deoxyguanosine (1), according to an embodiment of the invention. See FIG. 1.

$O^6$-Benzyl-5'-dimethoxytrityl)-2-deoxyguanosine (5). Nucleoside 4 is synthesized according to a known method (Luu et al., *Biochemistry* 2002, 41, 8689-8697). NaOH (1.0 M, 50 mL) is added to a solution of nucleoside 4 (3.93 g, 4.96 mmol) in CH$_3$CN (100 mL) and stirred at room temperature for 18 h. The reaction is neutralized with HCl (1.0 M) and extracted with CH$_2$Cl$_2$ (3×50 mL). The resulting organic layers are combined, dried with MgSO$_4$, filtered, and the solvent is removed under reduced pressure to yield 5 as a white solid (3.18 g, 97.2%). $^1$H NMR (DMSO-$d_6$) δ 7.94 (1H, s, H-8), 7.94-7.51 (2H, m, BnAr), 7.42-7.32 (5H, m, DMT Ar and Bn Ar), 7.26-7.15 (7H, m, DMT Ph and DMT Ar), 6.84-6.78 (4H, m, DMT Ph and DMT Ar), 6.46 (2H, br s, N$^2$H$_2$, D$_2$O exchangeable), 6.24 (1H, t, J=6.4, H-1'), 5.49 (2H, s, CH$_2$-Ph), 5.32 (1H, br d, J=4.4, 3'-OH, D$_2$O exchangeable), 4.39 (1H, ddd, J=9.6, J=4.4, J=4.4, H-3'), 3.93 (1H, dd, J=8.8, J=4.4, H-4'), 3.71 (3H, s, DMT-O—CH$_3$), 3.70 (3H, s, DMT-O—CH$_3$), 3.13 (2H, d, J=5.5, H-5'), 2.70 (1H, ddd, J=13.2, J=6.4, J=6.4, H-2'), 2.29 (1H, ddd, J=11.2, J=6.4, J=4.8, H-2').

$O^6$-Benzyl-3'-O-[γ-[α-[2-(trimethylsilyl)ethoxy]]-2-N-[2-(trimethylsilyl)-ethoxycarbonyl]folyl]-2'-deoxyguanosine (7). Folate 6 is synthesized according to a known method (Nomura et al., *J. Org. Chem.* 2000, 11, 5016-5021). 4-Dimethylaminopyridine (DMAP) (0.0324 g, 0.265 mmol) and 1,3-dicyclohexylcarbodiimide (DCC), (1.09 g, 5.30 mmol) are added to a solution of 6 (1.82 g, 2.65 mmol) in dichloromethane (75 mL) and stirred at room temperature for 1.5 h. Nucleoside 5 (1.75 g, 2.65 mmol) is then added to the solution and stirred for an additional 18 h. The solvent is removed under reduced pressure to yield a yellow foam. The solid foam is dissolved in EtOAc and filtered to remove insoluble dicyclohexylurea and dried under reduced pressure to afford a yellow solid. This solid is dissolved in 80% acetic acid (25 mL) and stirred for 30 min. Ethanol (250 mL) is added and the solvent is removed under reduced pressure to afford an orange foam which is purified by column chromatography (silica gel, 7:3:0.25 CH$_2$Cl$_2$:EtOAc:MeOH) to give 7 (1.1 g, 40.4%). $^1$H NMR (DMSO-$d_6$) δ 11.71 (2H, br s, folate N$^3$H and folate N$^2$H, exchanges with D$_2$O), 8.84 (1H, s, folate H-7), 8.26 (1H, br d, J=7.6, glu NH, exchanges with D$_2$O), 8.10 (1H, s, guanine H-8), 7.66 (2H, br d, J=8.8, pAB Ar), 7.50 (2H, br dd, J=8.4, J=1.6, Bn Ar), 7.42-7.32 (3H, m, Bn Ar), 7.03 (1H, t, J=6.0, folate 6-CH$_2$NH, exchanges with D$_2$O), 6.66 (2H, d, J=8.8, pAB Ar), 6.50 (2H, br s, guanine N$^2$H$_2$, exchanges with D$_2$O), 6.19 (1H, dd, J=9.2, J=5.6, H-1'), 5.50 (2H, s, CH$_2$-Ph), 5.32 (1H, br d, J=6.0, H-3'), 5.16 (1H, br t, J=5.6, 5'-OH, exchanges with D$_2$O), 4.59 (2H, br d, J=6.0, folate 6-CH$_2$NH, singlet in D$_2$O), 4.41 (1H, ddd, J=12.8, J=7.6, J=5.2, gluα-CH), 4.32-4.27 (2H, m, TMS-CH$_2$CH$_2$), 4.15-4.11 (2H, m, TMS-CH$_2$CH$_2$), 4.00 (1H, td, J=4.4, J=1.6, H-4'), 3.62-3.52 (2H, m, H-5'), 2.84 (1H, ddd, J=14.8, J=9.2, J=6.0, H-2'), 2.48 (2H, br t, J=7.6, gluγ-CH$_2$), 2.40 (1H, br dd, J=13.2, J=5.6, H-2'), 2.11 (1H, ddd, J=20.8, J=8.0, J=6.0, gluβ-CH$_{2a}$), 2.03-1.94 (1H, m, gluβ-CH$_{2b}$), 1.07-1.03 (2H, m, TMS-CH$_2$CH$_2$), 0.96-0.92 (2H, m, TMS-CH$_2$CH$_2$), 0.058 (9H, s, Si(CH$_3$)$_3$), 0.003 (9H, s, Si(CH$_3$)$_3$). MS m/z 1025.6 [M+H]$^+$; Anal. (C$_{47}$H$_{60}$N$_{12}$O$_{11}$Si$_2$) C, H, N.

$O^6$-Benzyl-3'-O-[γ-folyl]-2'-deoxyguanosine (1). Tetrabutylammonium fluoride (TBAF), (1.0 Min THF, 2.15 mL) is added to a solution of 7 (0.220 g, 0.215 mmol) dissolved in DMSO (2.15 mL) and stirred at room temperature for 2 h. Water (25 mL) is added to the reaction, and the pH of the solution is adjusted to 3 with HCl. The yellow precipitate is filtered off and suspended in 2:1 H$_2$O/MeOH (50 mL). NaHCO$_3$ (0.036 g, 0.430 mmol) is added to the suspension and stirred until the solid is completely dissolved (~2 h). The solution is acidified to pH 3 with HCl, and the resulting solid is filtered and dried under vacuum (0.161 g, 95.8%). UV (0.05 M phosphate, pH 7.4) λ$_{max}$=253 nm (ε=1.23×10$^4$), λ$_{max}$ 284 nm (ε=2.00×10$^4$), λ$_{max}$ 362 nm (ε=5.20×10$^3$). $^1$H NMR (DMSO-$d_6$) δ 12.54 (1H, br s, $CO_2H$ exchanges in $D_2O$), 11.48 (1H, br s, folate $N^3H$ exchanges in $D_2O$), 8.65 (1H, s, folate H-7), 8.14-8.13 (1H, m, glu NH, exchanges with $D_2O$), 8.10 (1H, s, guanine H-8), 7.65 (2H, br d, J=8.8, pAB Ar), 7.50 (2H, br dd, J=8.4, J=1.6, Bn Ar), 7.42-7.33 (3H, m, Bn Ar), 6.92 (3H, t, J=6.0, folate 6-$CH_2NH$ and folate $N^2H_2$, exchanges with $D_2O$), 6.66 (2H, d, J=8.8, pAB Ar), 6.50 (2H, br s, guanine $N^2H_2$, exchanges with $D_2O$), 6.19 (1H, dd, J=9.2, J=5.6, H-1'), 5.50 (2H, s, $CH_2$-Ph), 5.32 (1H, br d, J=6.0, H-3'), 5.16 (1H, br t, J=5.6, 5'-OH, exchanges with $D_2O$), 4.48 (2H, br d, J=5.2, folate 6-$CH_2NH$, singlet in $D_2O$), 4.40-4.35 (1H, m, gluα-CH), 4.01 (1H, td, J=4.0, J=1.2, H-4'), 3.57 (2H, br s, H-5'), 2.84 (1H, ddd, J=14.8, J=9.2, J=6.0, H-2'), 2.47 (2H, br t, J=7.2, gluγ-$CH_2$), 2.41 (1H, br dd, J=12.8, J=5.6, H-2'), 2.18-2.09 (1H, m, gluβ-$CH_{2a}$), 2.02-1.91 (1H, m, gluβ-$CH_{2b}$). MS m/z 781.3 $[M+H]^+$; Anal. ($C_{36}H_{36}N_{12}O_9 \cdot 1.6H_2O$) C, H, N.

Example 2

This example demonstrates a synthesis of $O^6$-benzyl-5'-O-[γ-folyl]-2"-deoxyguanosine (2), according to an embodiment of the invention. See FIG. 2.

$O^6$-Benzyl-3'-O-(t-butyldimethylsilyl)-5'-O-(4,4'-dimethoxytrityl)-$N^2$-phenoxyacetyl-2'-deoxyguanosine (8). Imidazole (0.607 g, 8.92 mmol) is added to a solution of 4 (1.77 g, 2.23 mmol) in DMF (6 mL) and stirred until completely dissolved. tert-Butyldimethylsilyl chloride (1.01 g, 6.70 mmol) is added and the reaction is stirred at room temperature for 18 h. The solvent is removed under reduced pressure, water (20 mL) is added to the residue and extracted with $CH_2Cl_2$ (3×30 mL). The organic extracts are combined, dried over $MgSO_4$, filtered, and the solvent is removed under reduced pressure. The resulting oil is purified by column chromatography (silica, 70:30 EtOAc:Hex) to yield 8 as a white solid (1.84 g, 90.9%). $^1$H NMR (DMSO-$d_6$) δ 10.69 (1H, br s, $N^2H$, exchanges with $D_2O$), 8.44 (1H, s, H-8), 7.60-7.57 (2H, m, Pac Ar), 7.46-7.38 (3H, m, Bn Ar), 7.35-7.29 (4H, m, Bn Ar and DMT Ar), 7.25-7.17 (7H, m, DMT Ph and DMT Ar), 7.10-6.94 (3H, m, Pac Ar), 6.83-6.77 (4H, m DMT Ar), 6.40 (1H, br dd, J=6.0, J=6.8, H-1'), 5.66 (2H, s, Pac-$CH_2$), 5.05 (1H, d, J=18.0, diastereotopic $CH_2$-Ph), 5.04 (1H, d, J=18.0, diastereotopic $CH_2$-Ph), 4.69 (1H, br dd, J=10.8, J=5.2, H-3'), 3.88 (1H, br dd, J=9.6, J=5.2, H-4'), 3.73 (6H, s, DMT-(O—$CH_3)_2$), 3.28-3.20 (2H, m, H-5'), 2.96 (1H, ddd, J=13.2, J=6.4, J=6.4, H-2'), 2.38 (1H, ddd, J=12.8, J=6.8, J=5.2, H-2'), 0.816 (9H, s, Si—$C(CH_3)_3$), 0.035 (3H, s, Si—$CH_3$), −0.031 (3H, s, Si—$CH_3$). Anal. ($C_{52}H_{57}N_5O_8Si$) C, H, N.

$O^6$-Benzyl-3'-O-(t-butyldimethylsilyl)-$N^2$-phenoxyacetyl-2'-deoxyguanosine (9). A solution of 3% TCA (67.8 mL, 19.9 mmol) in $CH_2Cl_2$ is added to a solution of 8 (4.51 g, 4.97 mmol) dissolved in $CH_2Cl_2$ (100 mL) and stirred at room temperature for 4 minutes. $Et_3N$ (2.77 mL, 19.9 mmol) is added to the solution, and the solvent is removed under reduced pressure. The resulting solid is purified by column chromatography (silica, 90:10 $CH_2Cl_2$:EtOAc) to afford 9 as an off-white foam (2.56, 85.0%). $^1$H NMR (DMSO-$d_6$) δ 10.69 (1H, s, $N^2H$, exchanges with $D_2O$), 8.47 (1H, s, H-8), 7.54 (2H, dd, J=8.4, J=1.6, PAc Ar), 7.42-7.34 (3H, m, Bn Ar), 7.31-7.26 (2H, m, Bn Ar), 6.97-6.92 (3H, m, PAc Ar), 6.33 (1H, t, J=6.8, H-1'), 5.63 (2H, s, $CH_2$-Ph), 5.04 (2H, s, Pac-$CH_2$), 4.94 (1H, t, J=5.4, 5'-OH, exchanges with $D_2O$), 4.60 (1H, ddd, J=5.6, J=2.8, J=2.8, H-3'), 3.84 (1H, ddd, J=4.8, J=2.8, H-4'), 3.57 (1H, ddd, J=11.6, J=5.6, H-5'), 3.51 (1H, J=11.2, J=5.2, J=4.8, H-5'), 2.82 (1H, ddd, J=13.2, J=6.0, J=2.0, H-2'), 2.28 (1H, ddd, J=13.2, J=6.0, J=3.2, H-2'), 0.875 (9H, s, Si—$C(CH_3)_3$), 0.094 (3H, s, Si—$CH_3$), 0.088 (3H, s, Si—$CH_3$). Anal. ($C_{31}H_{39}N_5O_6Si$) C, H, N.

$O^6$-Benzyl-3'-O-(t-butyldimethylsilyl)-2'-deoxyguanosine (10). NaOH (2 M, 21 mL, 42.3 mmol) is added to a solution of 9 (2.56 g, 4.23 mmol) dissolved in $CH_3CN$ (13 mL) and stirred at room temperature for 21 h. Water (20 mL) is added to the reaction and the pH is adjusted to 7 with HCl. The solution is extracted with $CH_2Cl_2$ (2×30 mL), and the organic extracts are combined, dried over $MgSO_4$, and filtered. The solvent is removed under reduced pressure to yield 10 as a white solid (1.86 g, 93.4%). $^1$H NMR (DMSO-$d_6$) δ 8.11 (1H, s, H-8), 7.51-7.48 (2H, m, Bn Ar), 7.42-7.33 (3H, m, Bn Ar), 6.50 (2H, br s, $N^2H_2$, exchanges with $D_2O$), 6.21 (1H, dd, J=8.0, J=6.0, 11-1'), 5.50 (2H, s, $CH_2$-Ph), 5.04 (1H, t, J=5.6, 5'-OH, exchanges with $D_2O$), 4.53 (1H, ddd, J=5.2, J=2.4, J=2.4, H-3'), 3.82 (1H, ddd, J=4.4, J=4.4, J=2.4, H-4'), 3.55 (H-1, ddd, J=11.6, J=5.2, J=5.2, H-5'), 3.49 (1H, ddd, J=11.6, J=5.2, J=4.8, H-5'), 2.70 (1H, ddd, J=13.2, J=8.0, J=5.6, H-2'), 2.21 (1H, ddd, J=12.8, J=5.6, J=2.4, H-2'), 0.90 (9H, s, Si—$C(CH_3)_3$), 0.11 (6H, s, Si—$(CH_3)_2$). Anal. ($C_{23}H_{33}N_5O_4Si$) C, H, N.

$O^6$-Benzyl-3'-O-(t-butyldimethylsilyl)-5'-O-[γ-[α-[2-(trimethylsilyl)ethoxy]]-2-N-[2-(trimethylsilyl)-ethoxycarbonyl]folyl]-2'-deoxyguanosine (11). 4-Dimethylaminopyridine (DMAP) (0.764 g, 6.25 mmol), 1-[3-(dimethylamino)propyl]-3-ethylcarbodiimide hydrochloride (EDC) (1.20 g, 6.25 mmol), and 10 (2.67 g, 5.68 mmol) are added to a solution of protected folate 6 (4.29 g, 6.25 mmol) in dichloromethane (180 mL) and stirred at room temperature for 3 h. Water (100 mL) is added to the solution, the organic layer is extracted off and subsequently dried over $MgSO_4$ and filtered. The solution is dried under reduced pressure and the resulting yellow foam is purified by column chromatography (silica gel, EtOAc) to afford 11 (2.62 g, 40.5%). $^1$H NMR (DMSO-$d_6$) δ 11.72 (2H, br s, folate $N^3H$ and $N^2H$, exchanges with $D_2O$), 8.84 (1H, s, folate H-7), 8.26 (1H, d, J=7.6, glu-NH, exchanges with $D_2O$), 8.09 (1H, s, guanine H-8), 7.66 (2H, d, J=8.8, pAB Ar), 7.50 (2H, br dd, J=8.4, J=1.6, Bn Ar), 7.43-7.33 (3H, m, Bn Ar), 7.04 (1H, t, J=6.2, folate 6-$CH_2NH$, exchanges with $D_2O$), 6.66 (2H, d, J=8.8, pAB Ar), 6.52 (2H, br s, guanine $N^2H_2$, exchanges with $D_2O$), 6.22 (1H, br t, J=7.0, H-1'), 5.50 (2H, s, $CH_2$-Ph), 4.59 (2H, d, J=6.0, folate 6-$CH_2$—NH, singlet in $D_2O$), 4.53 (1H, ddd, J=6.0, J=2.8, J=2.8, H-3'), 4.37 (1H, ddd, J=12.8, J=5.2, J=2.0, gluα-CH), 4.33-4.29 (2H, m, TMS-$CH_2CH_2$), 4.23 (1H, dd, J=11.6, J=6.0, H-5'), 4.16-4.10 (3H, m, TMS-$CH_2CH_2$ and H-5'), 3.96 (1H, ddd, J=6.0, J=6.0, J=6.0, H-4'), 2.83 (1H, ddd, J=7.6, J=3.6, J=2.8, H-2'), 2.44 (2H, br t, J=7.4, gluγ-$CH_2$), 2.25 (1H, ddd, J=13.6, J=6.0, J=3.6, H-2'), 2.12-2.03 (1H, m, gluβ-$CH_{2a}$), 1.99-1.91 (1H, m, gluβ-$CH_{2b}$), 1.08-1.04 (2H, m, -TMS$CH_2CH_2$), 0.94-0.90 (2H, m, -TMS$CH_2CH_2$), 0.86 (9H, s, Si—$C(CH_3)_3$), 0.080 (6H, s, Si—$(CH_3)_2$), 0.070 (9H, s, Si—$(CH_3)_3$), 0.012 (9H, s, Si—$(CH_3)_3$). Anal. ($C_{53}H_{74}N_{12}O_{11}Si_3$) C, H, N.

$O^6$-Benzyl-5'-O-[γ-folyl]-2'-deoxyguanosine (2). Tetrabutylammonium fluoride (TBAF) (1.0 M in THF, 6.71 mL) is added to 11 (0.510 g, 0.448 mmol) dissolved in DMSO (5.0 mL). The reaction is stirred at room temperature for 3 h. Water (140 mL) is added to the reaction, and the pH of the solution is adjusted to 3 with HCl. The yellow precipitate is filtered off and suspended in $H_2O$ (150 mL). $NaHCO_3$ (1M, 0.896 ml) is added to the suspension and stirred until the solid is completely dissolved (~2 h). The solution is acidified to pH 3 with HCl and the resulting solid is filtered (0.297 g, 85.0%). The crude product, dissolved in 0.1 M $NaHCO_3$ at [10 mg/mL], is purified on a Sephadex LH-20 column eluted with 0.1 M NaCl at a flow rate of 1 mL/min. UV absorption is continuously monitored at 280 nm and 10 mL fractions are collected. The combined fractions (110-140) are reduced to approximately 50 ml and the pH of the solution is adjusted to 3 with HCl. The resulting yellow precipitate is filtered and dried to afford 2 as a yellow solid (0.110 g, 31.5% overall yield). UV (0.05 M phosphate, pH 7.4) $\lambda_{max}$ 253 nm (c=1.23×10$^4$), $\lambda_{max}$=284 nm (c=2.00×10$^4$), $\lambda_{max}$ 362 nm (ε=5.20×10$^3$). $^1$H NMR (DMSO-d$_6$) δ 12.51 (1H, br s, CO$_2$H, exchanges with D$_2$O), 11.49 (1H, br s, folate N$^3$H, exchanges with D$_2$O), 8.64 (1H, s, folate H-7), 8.12 (1H, br d, J=6.4, glu-NH, exchanges with D$_2$O), 8.04 (1H, s, guanine H-8), 7.64 (2H, d, J=8.8, pAB Ar), 7.49 (2H, dd, J=8.4, J=1.6, Bn Ar), 7.41-7.32 (3H, m, Bn Ar), 6.92 (3H, br t, J=6.0, folate N$^2$H$_2$ and folate 6-CH$_2$NH, exchanges with D$_2$O), 6.64 (2H, d, J=8.8, pAB Ar), 6.51 (2H, br s, guanine N$^2$H$_2$, exchanges with D$_2$O), 6.21 (1H, t, J=6.8, H-1), 5.49 (2H, s, CH$_2$-Ph), 5.44 (1H, br s, 3'-OH, exchanges with D$_2$O), 4.48 (2H, d, J=5.6, folate 6-CH$_2$—NH, singlet in D$_2$O, 4.40-4.37 (1H, m, H-3'), 4.35-4.29 (1H, m, gluα-CH), 4.24 (1H, dd, J=11.6, J=4.8, H-5'), 4.13 (1H, dd, J=11.6, J=6.4, H-5'), 3.97-3.93 (1H, m, H-4'), 2.70 (1H, ddd, J=7.6, J=6.4, J=6.4, H-2'), 2.41 (2H, br t, J=7.6, gluγ-CH$_2$), 2.25 (1H, ddd, J=13.2, J=6.0, J=3.6, H-2'), 2.11-2.05 (1H, m, gluβ-CH$_{2a}$), 1.98-1.90 (1H, m, gluβ-CH$_{2b}$). MS m/z 781.3 [M+H]$^+$; Anal. (C$_{36}$H$_{36}$N$_{12}$O$_9$·1.5H$_2$O) C, H, N.

Example 3

This example demonstrates a synthesis of O$^6$-[4-[(γ-folyl)-oxymethyl]benzyl]guanine (3), according to an embodiment of the invention. See FIG. 3.

O$^6$-[4-[γ-[α-[2-(trimethylsilyl)ethoxy]]-2-N-[2-(trimethylsilyl)-ethoxycarbonyl]folyl]-oxymethyl]benzyl]guanine (13). O$^6$-[4-(Hydroxymethyl)benzyl]guanine (12) is synthesized as described by a known method (Chae et al., *J. Med. Chem.* 1994, 37, 342-347). Bis-silyl protected folic acid 6, (600 mg, 0.88 mmol), 12 (270 mg, 1.0 mmol) and 4-dimethylamoinopyridine (DMAP) (109 mg, 0.90 mmol) are combined in 15 ml of N,N-dimethylformamide. 1-[3-(Dimethylamino)-propyl]-3-ethylcarbodiimide hydrochloride (EDC), (173 mg, 0.9 mmol) is added and the reaction is stirred at room temperature for two hours. The solvent is evaporated under reduced pressure. The residue is dissolved in 100 ml of dichloromethane and extracted with an equal volume of 0.05 M HCl in water followed by pure water. The above extractions can give emulsions that require centrifugation to separate. The dichloromethane is then evaporated under reduced pressure. The resulting material is purified by column chromatography (silica gel, 19:1 chloroform:methanol). Upon evaporation of the solvent under reduced pressure, the desired bis-silyl protected product 13 is isolated as a yellow solid (300 mg, 36%). $^1$H NMR (Me$_2$SO-d$_6$) with no TMS standard. δ 12.4 (1H, br s, guanine N$^9$H, exchangeable with D$_2$O), 11.7 (2H, br s, folate N$^3$H and folate N$^2$H, exchangeable with D$_2$O), 8.83 (1H, s, folate H-7), 8.24 (1H, d, J=7.6, glu-NH, exchangeable with D$_2$O), 7.81 (1H, s, guanine H-8), 7.64 (2H, d, J=8.4, pAB Ar), 7.48 (2H, d, J=8.0, Bn Ar), 7.35 (2H, d, J=8.0, Bn Ar), 7.03 (1H, t, J=6.0, folate 6-CH$_2$—NH, exchangeable with D$_2$O), 6.65 (2H, d, J=8.4, pAB Ar), 6.28 (2H, s, guanine N$^2$H$_2$, exchangeable with D$_2$O), 5.47 (2H, s, benzyl-CH$_2$-guanine), 5.08 (2H, s, benzyl-CH$_2$-folate), 4.58 (2H, d, J=5.6, folate 6-CH$_2$—NH, singlet in D$_2$O), 4.36 (1H, ddd, J=12.4, J=7.6, J=5.2, gluα-CH), 4.31-4.27 (2H, m, TMS-CH$_2$CH$_2$), 4.13-4.09 (2H, m, TMS-CH$_2$CH$_2$), 2.47 (2H, t, J=7.6, gluγ-CH$_2$), 2.13-2.04 (1H, m, gluβ-CH$_{2a}$), 2.02-1.94 (1H, m, gluβ-CH$_{2b}$), 1.04 (2H, ddd, J=8.8, J=6.8, J=4.0, TMS-CH$_2$CH$_2$), 0.92 (2H, ddd, J=8.4, J=6.8, J=4.4, TMS-CH$_2$CH$_2$), 0.05 (9H, s, TMS-CH$_3$), 0.01 (9H, s, TMS-CH$_3$). MS m/z 939.4 [M+H]$^+$.

O$^6$-[4-[(γ-folyl)-oxymethyl]benzyl]guanine (3). The above bis-protected O$^6$-[4-(hydroxymethyl)benzyl]guanine γ-folate ester 13, (290 mg, 0.31 mmol) is dissolved in 45 ml of dimethyl sulfoxide. Tetrabutylammonium fluoride (TBAF), (1 M in THF, 5 ml) is added, and the reaction is stirred for two hours at room temperature. The reaction is terminated with the addition of 450 ml of water and the suspension is acidified to pH 3 with HCl. Centrifugation of the resulting gelatinous mixture pellets the product. The pellet is dissolved in 100 ml of 1 mM sodium bicarbonate and precipitated by acidifying to pH 3 with HCl. The material is then repeatedly washed by suspending in water and pelleting by centrifugation prior to final drying under high vacuum to give 3 as a yellow powder (210 mg, 97%). UV in 0.1 M HCl, $\lambda_{max}$ 290 nm (c=2.95×10$^4$) and 364 nm (c=2.90×10$^3$), at pH 7 (0.05 M phosphate buffer) $\lambda_{max}$ 283 nm (ε=3.23×10$^4$) and 347 nm (c=6.60×10$^3$), in 0.1 M NaOH, $\lambda_{max}$ 256 nm (e=2.79×10$^4$), 285 nm (c=3.16×10$^4$) and 366 nm (ε=8.30×10$^3$), with decomposition in acid and base. $^1$H (Me$_2$SO-d$_6$). δ 12.4 (2H, br s, guanine N$^9$H and folic acid CO$_2$H, exchangeable with D$_2$O), 11.5 (1H, br s, folate N$^3$H, exchangeable with D$_2$O), 8.65 (1H, s, folate H-7), 8.13 (1H, d, J=7.6, glu-NH, exchangeable with D$_2$O), 7.82 (1H, s, guanine H-8), 7.65 (2H, d, J=8.8, pAB Ar), 7.48 (2H, d, J=8.0, Bn Ar), 7.36 (2H, d, J=8.0, Bn Ar), 6.94 (1H, t, J=6.0, folate 6-CH$_2$—NH, exchanges with D$_2$O), 6.90 (2H, br s, folate N$^2$H$_2$, exchanges with D$_2$O), 6.64 (2H, d, J=8.8, pAB Ar), 6.30 (2H, s, guanine N$^2$H$_2$, exchangeable with D$_2$O), 5.48 (2H, s, benzyl-CH$_2$-guanine), 5.08 (2H, s, benzyl-CH$_2$-folate), 4.48 (2H, d, J=6.0, folate 6-CH$_2$—NH, singlet in D$_2$O), 4.35 (1H, ddd, J=12.8, J=8.0, J=4.8, gluα-CH), 2.47 (2H, t, J=8.0, gluγ-CH$_2$), 2.15-2.06 (1H, m, gluβ-CH$_{2a}$) 2.01-1.91 (1H, m, gluβ-CH$_{2b}$). MS m/z 695.2 [M+H]$^+$. Anal. (C$_{32}$H$_{30}$N$_{12}$O$_7$·1H$_2$O) C, H, N.

Example 4

This example demonstrates the conversion of ester compounds of the present invention to folate.

Cells are trypsinized, washed with Hank's balanced salt solution, counted and pelleted. On ice, the cell pellets are resuspended in 50 mM sodium phosphate, 5 mM DTT, pH 7.4 at a concentration of 10$^8$ cells/ml and disrupted by sonication. The sonicated cells are centrifuged at 12,000×g for 10 min and the supernatant is removed. Complete mini protease inhibitor (Roche, Mannheim Germany) is added as directed by the supplier. Lysate total protein concentration is determined, and the lysates are frozen until used at −20° C. Reactions (600 μL), containing one of the ester substrates (200 μM) and 2 mg of lysate protein in 50 mM phosphate buffer (pH 7.4) are incubated at 37° C. At various times 50 μL, are removed for analysis by HPLC. The amount of folic acid liberated is used to determine the extent of ester hydrolysis. The results are summarized in FIG. 4.

Figure 4A:
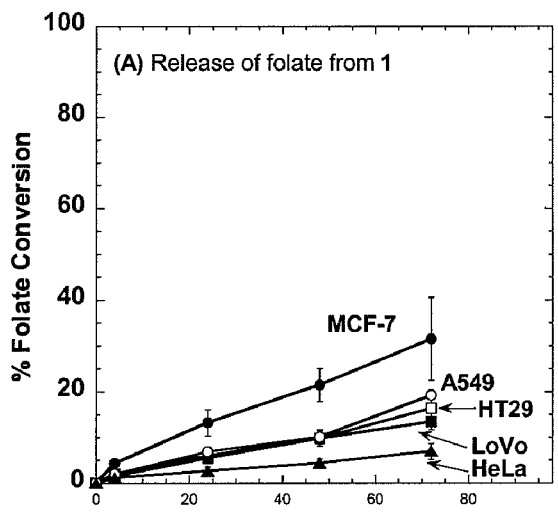
FIGS. 4A, 4B, and 4C are for compounds 1, 2, and 3, respectively.
Figure 4B:
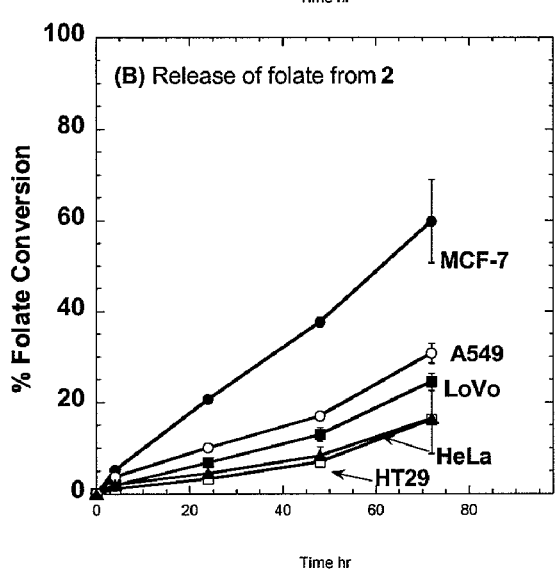
Figure 4C:
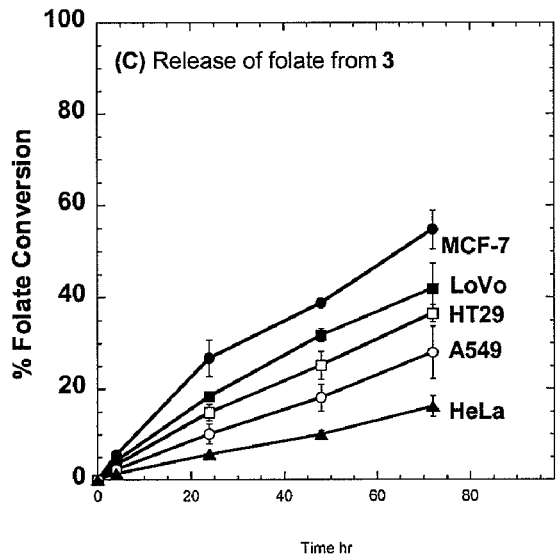

Compounds 1-3 are relatively stable when incubated in neutral solution. The rate of release of folate is about 2.2% per day from 1; 3.2% per day from 2; and 0.9% per day from 3. Extracts from a variety of human tumor cells are able to release folate from 1, 2, and 3 (FIGS. 4A, 4B, and 4C). The extent of conversion to folate by human tumor cell extracts can vary slightly according to the cell type with MCF-7 cells showing the highest rate of conversion.

Example 5

This example demonstrates the inactivation of purified recombinant human alkyltransferase in an embodiment of the invention.

$ED_{50}$ values for the inactivation of purified human alkyltransferase in vitro are obtained as previously described (Nelson et al., *J. Med. Chem.* 2004, 47, 3887-3891 and Pegg et al., *Biochem. Pharmacol.* 1997, 53, 1559-1564). Purified recombinant human alkyltransferase is incubated with different concentrations of prodrugs in 0.5 mL of reaction buffer (50 mM Tris-HCl, pH 7.6, 0.1 mM EDTA, 5.0 mM dithiothreitol) containing 50 μg of hemocyanin or 10 μg calf thymus DNA for 30 min at 37° C. The results are summarized in Table 1.

TABLE 1

Inactivation of purified human alkyltransferase in vitro

| Compound | $ED_{50}$ for inactivation of alkyltransferase (μM) * | |
|---|---|---|
| | −DNA | +DNA |
| $O^6$-benzylguanine [a] | 0.3 | 0.1 |
| $O^6$-benzyl-2'-deoxyguanosine [b] | 2.0 | 40.0 |
| 1 | 0.016 ± 0.002 | 0.68 ± 0.02 |
| 2 | 0.64 ± 0.05 | 3.06 ± 0.18 |
| 3 | 0.70 | 0.24 |
| 12 [c] | 0.4 | 0.1 |

[a] Previously published in Pegg et al., Biochem. Pharmacol. 1997, 53, 1559-1564 and Dolan et al., Proc. Natl. Acad. Sci. U.S.A. 1990, 87, 5368-5372;
[b] Previously published in Moschel et al., J. Med. Chem. 1992, 35, 4486-4491 and Pegg et al., Biochem. Pharmacol. 1997, 53, 1559-1564;
[c] Previously published in Chae et al., J. Med. Chem. 1994, 37, 342-347 and Ciocco et al., Cancer Res. 1995, 55, 4085-4091
* $ED_{50}$ values are calculated from graphs of the percentage of remaining alkyltransferase activity against inhibitor concentration. Experiments where an S.D. is shown are repeated 3-5 times and the mean is shown. Other values are the mean of two experiments.

Both 1 and 2 are more active than $O^6$-benzyl-2'-deoxyguanosine itself in the inactivation of alkyltransferase (Table 1). The 3' ester (1) is an extremely potent alkyltransferase inactivator with an $ED_{50}$ value in the absence of DNA of 16 nM, which is 100-times lower than the parent $O^6$-benzyl-2'-deoxyguanosine and 10 times lower than $O^6$-benzylguanine. When DNA is present, the $ED_{50}$ value of 1 is increased to 0.68 μM but this is still much less than that of $O^6$-benzyl-2'-deoxyguanosine itself (40 μM).

The 5' ester (2) is also a potent inactivator of alkyltransferase that is more effective in the absence of DNA but it is less active than 1 with an $ED_{50}$ value of 640 nM compared to 16 nM for 1 (Table 1). When DNA is present, the $ED_{50}$ of 2 increased 5-fold to about 3 μM. These results suggest that the addition of a folate moiety increases the ability of $O^6$-benzyl-2'-deoxyguanosine to bind to human alkyltransferase. Compound 3, the folic acid γ ester of 12 is slightly less effective than the free base parent in the inactivation of alkyltransferase (Table 1).

Example 6

This example demonstrates an ability of compounds in accordance with an embodiment of the invention to sensitize cells to killing by 1,3-bis(2-chloroethyl)-1-nitrosourea (BCNU).

KB, HT29 and A549 cells are grown in RPMI 1640 medium or in RPMI medium lacking folate in the presence of 10% fetal bovine serum. The effect of alkyltransferase inactivators on the sensitivity of cells to BCNU is determined using a colony-forming assay (Wei et al., *J. Med. Chem.* 2005, 48, 256-261; Nelson et al., *J. Med. Chem.* 2004, 47, 3887-3891; Chae et al., *J. Med. Chem.* 1994, 37, 342-347; and Dolan et al., *Proc. Natl. Acad. Sci. U.S.A.* 1990, 87, 5368-5372). Cells are plated at a density of $10^6$ in 25 cm² flasks and 24 h later are incubated with different concentrations of potential inhibitors for 2-8 h as indicated before exposure to 20 or 40 μM BCNU for 2 h as previously described (Wei et al., *J. Med. Chem.* 2005, 48, 256-261; Nelson et al., *J. Med. Chem.* 2004, 47, 3887-3891). After 2 h, the medium is replaced with fresh medium containing the drug but no BCNU and the cells are left to grow for an additional 16-18 h. The cells are then replated at densities of 250-1000 cells per 25 cm² flask and grown for 8 days until discrete colonies have formed. The colonies are washed with 0.9% saline solution, stained with 0.5% crystal violet in ethanol, and counted. The results are summarized in FIG. 5. Both 1 and 2 are able to sensitize HT29 cells to killing by BCNU.

In order to test whether compounds 1-3 enter cells via the folate receptor mechanism, studies are carried out to examine the killing by BCNU of A549, HT29 and KB cells grown for 48 h in the absence of folate prior to the addition of the inhibitors (FIG. 6). The inhibitors are added for 8 h prior to treatment with BCNU to allow increased time for alkyltransferase inactivation to occur but other experiments (not shown) with 2 h or 4 h drug exposure times gave similar results. Approximately the same degree of sensitization is seen with the three cell lines even though A549 cells have very low levels of folate receptors and KB cells have a very high folate receptor carrier activity. This suggests that the compounds are not taken up via a folate receptor mediated mechanism. This is supported by comparison of the effects of 8 h exposure to drugs on HT29 cells grown in the folate free medium shown in FIG. 6B with the effects of 2 h exposure on HT29 cells grown in the folate containing medium in FIG. 5. There is little difference in the effect under the two conditions.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments can become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all pos-

The invention claimed is:

1. A compound of formula (I):

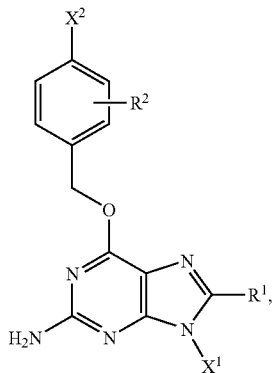

(I)

wherein
X¹ is selected from the group consisting of

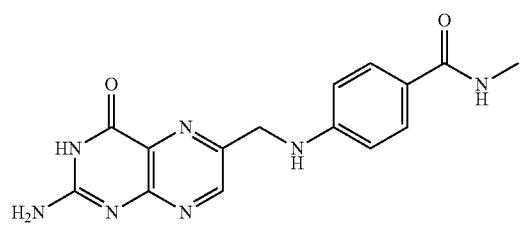

and

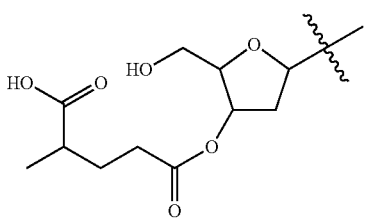

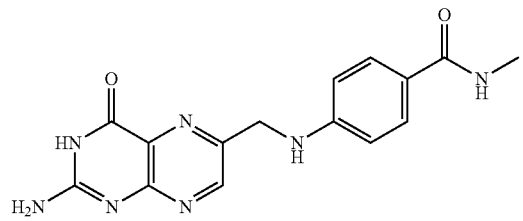

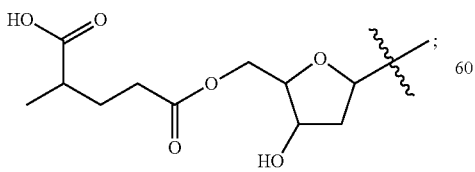

hydrogen, $C_1$-$C_6$ alkyl, $C_1$-$C_6$ aminoalkyl, $C_1$-$C_6$ hydroxyalkyl, $C_1$-$C_6$ alkylaminoalkyl, $C_1$-$C_6$ dialkylaminoalkyl, $C_1$-$C_6$ cyanoalkyl, $C_1$-$C_6$ carbamoylalkyl, $C_1$-$C_6$ pivaloylalkyl, $C_1$-$C_6$ alkylcarbonyloxy $C_1$-$C_6$ alkyl, $C_1$-$C_6$ alkoxycarbonylalkyl, ribose, 2'-deoxyribose, the conjugate acid form of a $C_1$-$C_6$ carboxyalkyl, and the carboxylate anion of a $C_1$-$C_6$ carboxyalkyl as the sodium salt;

X² is selected from the group consisting of

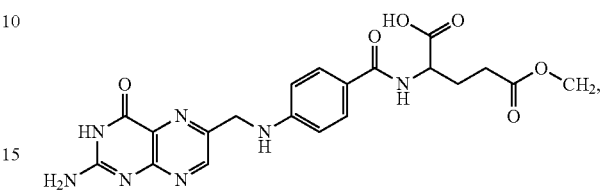

hydrogen, halo, hydroxy, a $C_1$-$C_6$ alkyl, aryl, a $C_1$-$C_6$ alkyl substituted aryl, nitro, a polycyclic aromatic $C_1$-$C_6$ alkyl containing 2-4 aromatic rings, a $C_3$-$C_8$ cycloalkyl, a $C_2$-$C_6$ alkenyl, a $C_2$-$C_6$ alkynyl, a $C_1$-$C_6$ hydroxyalkyl, a $C_1$-$C_8$ alkoxy, a $C_2$-$C_8$ alkoxyalkyl, aryloxy, acyloxy, an acyloxy-$C_1$-$C_6$ alkyl, amino, a $C_1$-$C_6$ alkylamino, a $C_1$-$C_6$ dialkylamino, acylamino, ureido, thioureido, carboxy, a carboxy-$C_1$-$C_6$ alkyl, cyano, a $C_1$-$C_6$ cyanoalkyl, formyl, acyl, a di-$C_1$-$C_6$ alkoxymethyl, an amino-$C_1$-$C_6$ alkyl, and $SO_nR^a$, wherein n is 0, 1, 2, or 3 and $R^a$ is H, a $C_1$-$C_6$ alkyl, or aryl;

R¹ is selected from the group consisting of hydrogen, halo, $C_1$-$C_4$ alkyl, $C_1$-$C_4$ hydroxyalkyl, mercapto, $C_1$-$C_4$ alkylthio, trifluoromethylthio, $C_1$-$C_4$ thioacyl, hydroxy, $C_1$-$C_4$ alkoxy, trifluoromethoxy, methanesulfonyloxy, trifluoromethanesulfonyloxy, $C_1$-$C_4$ acyloxy, amino, $C_1$-$C_4$ aminoalkyl, $C_1$-$C_4$ alkylamino, $C_1$-$C_4$ dialkylamino, trifluoromethylamino, ditrifluoromethylamino, aminomethanesulfonyl, $C_1$-$C_4$ aminoacyl, aminotrifluoromethylcarbonyl, formylamino, nitro, nitroso, $C_1$-$C_4$ alkyldiazo, $C_5$-$C_6$ aryldiazo, trifluoromethyl, $C_1$-$C_4$ haloalkyl, $C_1$-$C_4$ cyanoalkyl, cyano, $C_1$-$C_4$ alkyloxycarbonyl, $C_1$-$C_4$ alkylcarbonyl, phenyl, phenylcarbonyl, formyl, $C_1$-$C_4$ alkoxymethyl, phenoxymethyl, $C_2$-$C_4$ vinyl, $C_2$-$C_4$ ethynyl, and $SO_mR^b$, wherein m is 0, 1, 2, or 3 and $R^b$ is hydrogen, $C_1$-$C_4$ alkyl, amino, or aryl;

R² is selected from the group consisting of hydrogen, halo, hydroxy, a $C_1$-$C_6$ alkyl, aryl, a $C_1$-$C_6$ alkyl substituted aryl, nitro, a polycyclic aromatic $C_1$-$C_6$ alkyl containing 2-4 aromatic rings, a $C_3$-$C_8$ cycloalkyl, a $C_2$-$C_6$ alkenyl, a $C_2$-$C_6$ alkynyl, a $C_1$-$C_6$ hydroxyalkyl, a $C_1$-$C_8$ alkoxy, a $C_2$-$C_8$ alkoxyalkyl, aryloxy, acyloxy, an acyloxy-$C_1$-$C_6$ alkyl, amino, a $C_1$-$C_6$ alkylamino, a $C_1$-$C_6$ dialkylamino, acylamino, ureido, thioureido, carboxy, a carboxy-$C_1$-$C_6$ alkyl, cyano, a $C_1$-$C_6$ cyanoalkyl, formyl, acyl, a di-$C_1$-$C_6$ alkoxymethyl, a $C_1$-$C_6$ aminoalkyl, and $SO_pR^c$, wherein p is 0, 1, 2, or 3 and $R^c$ is H, a $C_1$-$C_6$ alkyl, or aryl;

or a pharmaceutically acceptable salt thereof;

provided that at least one of X¹ and X² is a folate residue and the other of X¹ and X² is a moiety other than a folate residue.

2. The compound or pharmaceutically acceptable salt of claim 1, wherein
$X^1$ is selected from the group consisting of

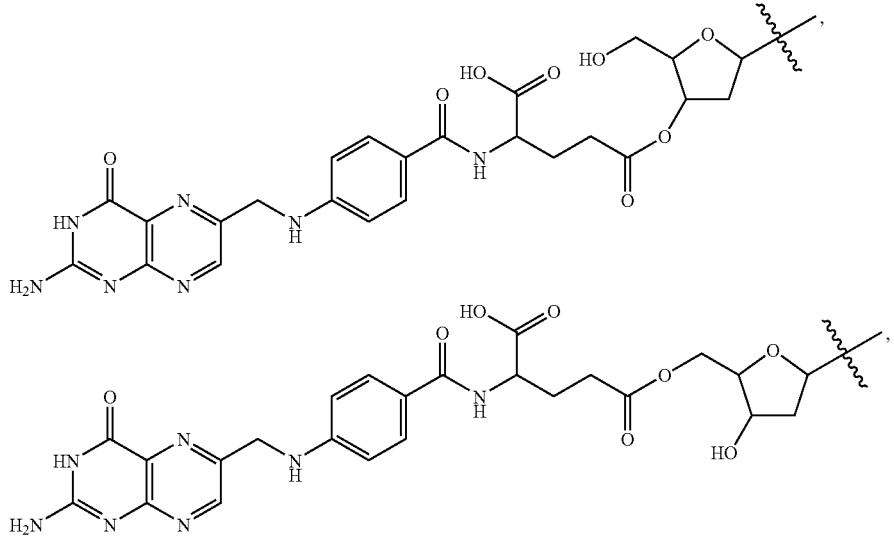

$X^2$ is selected from the group consisting of hydrogen, halo, hydroxy, a $C_1$-$C_6$ alkyl, aryl, a $C_1$-$C_6$ alkyl substituted aryl, nitro, a polycyclic aromatic $C_1$-$C_6$ alkyl containing 2-4 aromatic rings, a $C_3$-$C_8$ cycloalkyl, a $C_2$-$C_6$ alkenyl, a $C_2$-$C_6$ alkynyl, a $C_1$-$C_6$ hydroxyalkyl, a $C_1$-$C_8$ alkoxy, a $C_2$-$C_8$ alkoxyalkyl, aryloxy, acyloxy, an acyloxy-$C_1$-$C_6$ alkyl, amino, a $C_1$-$C_6$ alkylamino, a $C_1$-$C_6$ dialkylamino, acylamino, ureido, thioureido, carboxy, a carboxy-$C_1$-$C_6$ alkyl, cyano, a $C_1$-$C_6$ cyanoalkyl, formyl, acyl, a di-$C_1$-$C_6$ alkoxymethyl, an amino-$C_1$-$C_6$ alkyl, and $SO_nR^a$, wherein n is 0, 1, 2, or 3 and $R^a$ is H, a $C_1$-$C_6$ alkyl, or aryl;

$R^1$ is selected from the group consisting of hydrogen, halo, $C_1$-$C_4$ alkyl, $C_1$-$C_4$ hydroxyalkyl, mercapto, $C_1$-$C_4$ alkylthio, trifluoromethylthio, $C_1$-$C_4$ thioacyl, hydroxy, $C_1$-$C_4$ alkoxy, trifluoromethoxy, methanesulfonyloxy, trifluoromethanesulfonyloxy, $C_1$-$C_4$ acyloxy, amino, $C_1$-$C_4$ aminoalkyl, $C_1$-$C_4$ alkylamino, $C_1$-$C_4$ dialkylamino, trifluoromethylamino, ditrifluoromethylamino, aminomethanesulfonyl, $C_1$-$C_4$ aminoacyl, aminotrifluoromethylcarbonyl, formylamino, nitro, nitroso, $C_1$-$C_4$ alkyldiazo, $C_5$-$C_6$ aryldiazo, trifluoromethyl, $C_1$-$C_4$ haloalkyl, $C_1$-$C_4$ cyanoalkyl, cyano, $C_1$-$C_4$ alkyloxycarbonyl, $C_1$-$C_4$ alkylcarbonyl, phenyl, phenylcarbonyl, formyl, $C_1$-$C_4$ alkoxymethyl, phenoxymethyl, $C_2$-$C_4$ vinyl, $C_2$-$C_4$ ethynyl, and $SO_mR^b$, wherein m is 0, 1, 2, or 3 and $R^b$ is hydrogen, $C_1$-$C_4$ alkyl, amino, or aryl;

$R^2$ is selected from the group consisting of hydrogen, halo, hydroxy, a $C_1$-$C_6$ alkyl, aryl, a $C_1$-$C_6$ alkyl substituted aryl, nitro, a polycyclic aromatic $C_1$-$C_6$ alkyl containing 2-4 aromatic rings, a $C_3$-$C_8$ cycloalkyl, a $C_2$-$C_6$ alkenyl, a $C_2$-$C_6$ alkynyl, a $C_1$-$C_6$ hydroxyalkyl, a $C_1$-$C_8$ alkoxy, a $C_2$-$C_8$ alkoxyalkyl, aryloxy, acyloxy, an acyloxy-$C_1$-$C_6$ alkyl, amino, a $C_1$-$C_6$ alkylamino, a $C_1$-$C_6$ dialkylamino, acylamino, ureido, thioureido, carboxy, a carboxy-$C_1$-$C_6$ alkyl, cyano, a $C_1$-$C_6$ cyanoalkyl, formyl, acyl, a di-$C_1$-$C_6$ alkoxymethyl, a $C_1$-$C_6$ aminoalkyl, and $SO_pR^c$, wherein p is 0, 1, 2, or 3 and $R^c$ is H, a $C_1$-$C_6$ alkyl, or aryl.

3. The compound or pharmaceutically acceptable salt of claim 1, wherein $X^1$ is selected from the group consisting of hydrogen, $C_1$-$C_6$ alkyl, $C_1$-$C_6$ aminoalkyl, $C_1$-$C_6$ hydroxyalkyl, $C_1$-$C_6$ alkylaminoalkyl, $C_1$-$C_6$ dialkylaminoalkyl, $C_1$-$C_6$ cyanoalkyl, $C_1$-$C_6$ carbamoylalkyl, $C_1$-$C_6$ pivaloylalkyl, $C_1$-$C_6$ alkylcarbonyloxy $C_1$-$C_6$ alkyl, $C_1$-$C_6$ alkoxycarbonylalkyl, ribose, 2'-deoxyribose, the conjugate acid form of a $C_1$-$C_6$ carboxyalkyl, and the carboxylate anion of a $C_1$-$C_6$ carboxyalkyl as the sodium salt;

$X^2$ is

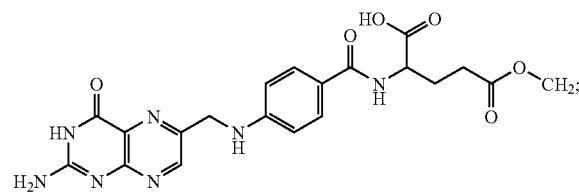

$R^1$ is selected from the group consisting of hydrogen, halo, $C_1$-$C_4$ alkyl, $C_1$-$C_4$ hydroxyalkyl, mercapto, $C_1$-$C_4$ alkylthio, trifluoromethylthio, $C_1$-$C_4$ thioacyl, hydroxy, $C_1$-$C_4$ alkoxy, trifluoromethoxy, methanesulfonyloxy, trifluoromethanesulfonyloxy, $C_1$-$C_4$ acyloxy, amino, $C_1$-$C_4$ aminoalkyl, $C_1$-$C_4$ alkylamino, $C_1$-$C_4$ dialkylamino, trifluoromethylamino, ditrifluoromethylamino, aminomethanesulfonyl, $C_1$-$C_4$ aminoacyl, aminotrifluoromethylcarbonyl, formylamino, nitro, nitroso, $C_1$-$C_4$ alkyldiazo, $C_5$-$C_6$ aryldiazo, trifluoromethyl, $C_1$-$C_4$ haloalkyl, $C_1$-$C_4$ cyanoalkyl, cyano, $C_1$-$C_4$ alkyloxycarbonyl, $C_1$-$C_4$ alkylcarbonyl, phenyl, phenylcarbonyl, formyl, $C_1$-$C_4$ alkoxymethyl, phenoxymethyl, $C_2$-$C_4$ vinyl, $C_2$-$C_4$ ethynyl, and $SO_mR^b$, wherein m is 0, 1, 2, or 3, and $R^b$ is hydrogen, $C_1$-$C_4$ alkyl, amino, or aryl;

$R^2$ is selected from the group consisting of hydrogen, halo, hydroxy, a $C_1$-$C_6$ alkyl, aryl, a $C_1$-$C_6$ alkyl substituted aryl, nitro, a polycyclic aromatic $C_1$-$C_6$ alkyl containing 2-4 aromatic rings, a $C_3$-$C_8$ cycloalkyl, a $C_2$-$C_6$ alkenyl, a $C_2$-$C_6$ alkynyl, a $C_1$-$C_6$ hydroxyalkyl, a $C_1$-$C_8$ alkoxy, a $C_2$-$C_8$ alkoxyalkyl, aryloxy, acyloxy, an acyloxy-$C_1$-$C_6$ alkyl, amino, a $C_1$-$C_6$ alkylamino, a $C_1$-$C_6$ dialkylamino, acylamino, ureido, thioureido, carboxy, a carboxy-$C_1$-$C_6$ alkyl, cyano, a $C_1$-$C_6$ cyanoalkyl, formyl, acyl, a di-$C_1$-$C_6$ alkoxymethyl, a $C_1$-$C_6$ aminoalkyl, and $SO_pR^c$, wherein p is 0, 1, 2, or 3, and $R^c$ is H, a $C_1$-$C_6$ alkyl, or aryl.

4. The compound or pharmaceutically acceptable salt of claim 1, wherein $R^1$ is hydrogen, halo, $C_1$-$C_4$ alkyl, $C_1$-$C_4$ hydroxyalkyl, mercapto, $C_1$-$C_4$ alkylthio, hydroxy, $C_1$-$C_4$ alkoxy, amino, $C_1$-$C_4$ aminoalkyl, $C_1$-$C_4$ alkylamino, $C_1$-$C_4$ dialkylamino, nitro, $C_1$-$C_4$ haloalkyl, $C_1$-$C_4$ cyanoalkyl, cyano, phenyl, phenylcarbonyl, or $C_1$-$C_4$ alkoxymethyl.

5. The compound or pharmaceutically acceptable salt of claim 1, wherein $R^2$ is hydrogen, halo, hydroxy, a $C_1$-$C_6$ alkyl, aryl, nitro, a $C_1$-$C_6$ hydroxyalkyl, a $C_1$-$C_8$ alkoxy, a aryloxy, amino, a $C_1$-$C_6$ alkylamino, a $C_1$-$C_6$ dialkylamino, carboxy, a carboxy-$C_1$-$C_6$ alkyl, cyano, a $C_1$-$C_6$ cyanoalkyl, or a $C_1$-$C_6$ aminoalkyl.

6. The compound or pharmaceutically acceptable salt of claim 1, wherein $X^2$ is hydrogen, halo, hydroxy, a $C_1$-$C_6$ alkyl, aryl, nitro, a $C_1$-$C_6$ hydroxyalkyl, a $C_1$-$C_8$ alkoxy, a aryloxy, amino, a $C_1$-$C_6$ alkylamino, a $C_1$-$C_6$ dialkylamino, carboxy, a carboxy-$C_1$-$C_6$ alkyl, cyano, a $C_1$-$C_6$ cyanoalkyl, or a $C_1$-$C_6$ aminoalkyl.

7. The compound or pharmaceutically acceptable salt of claim 1, wherein $X^1$ is selected from the group consisting of hydrogen, $C_1$-$C_6$ alkyl, $C_1$-$C_6$ aminoalkyl, $C_1$-$C_6$ hydroxyalkyl, $C_1$-$C_6$ alkylaminoalkyl, $C_1$-$C_6$ dialkylaminoalkyl, and $C_1$-$C_6$ cyanoalkyl.

8. The compound or pharmaceutically acceptable salt of claim 7, wherein $X^1$ is hydrogen.

9. The compound or pharmaceutically acceptable salt of claim 1, which is

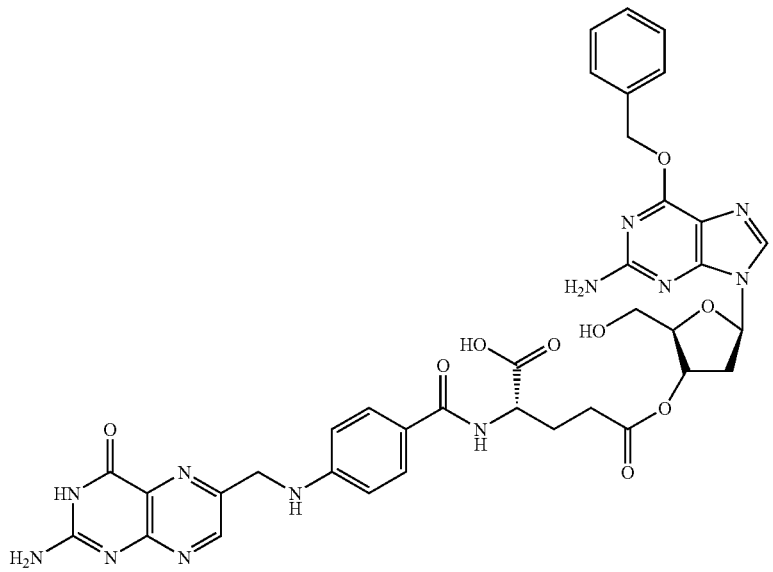

or pharmaceutically acceptable salt thereof.

10. The compound or pharmaceutically acceptable salt of claim 1, which is

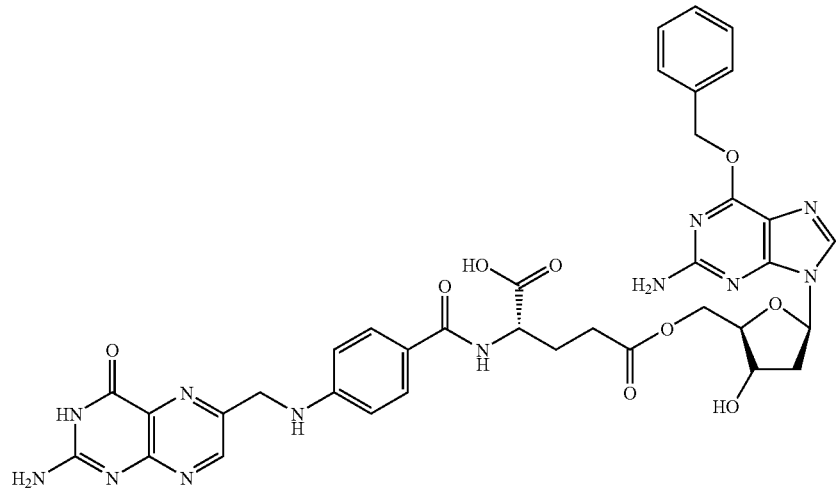

or pharmaceutically acceptable salt thereof.

11. The compound of claim 1, which is

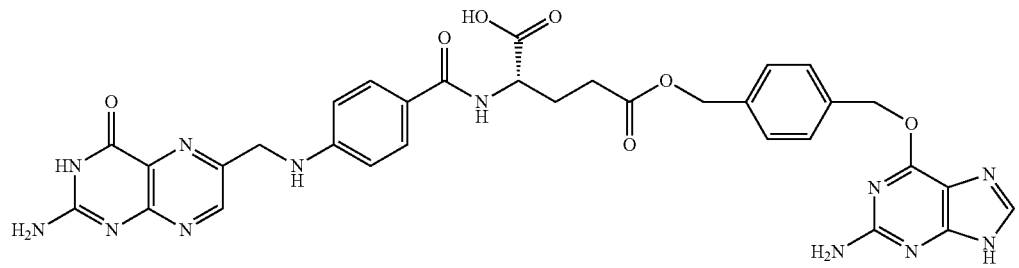

or pharmaceutically acceptable salt thereof.

12. A pharmaceutical composition comprising (a) a compound or pharmaceutically acceptable salt of claim 1 and (b) a pharmaceutically acceptable carrier.

13. A method of enhancing the chemotherapeutic treatment of tumor cells in a mammal with an antineoplastic alkylating agent that causes cytotoxic lesions at the $O^6$-position of guanine, which method comprises administering to the mammal an effective amount of the compound or pharmaceutically acceptable salt of claim 1, and administering to the mammal an effective amount of an antineoplastic alkylating agent which causes cytotoxic lesions at the $O^6$-position of guanine.

14. The method of claim 13, wherein the mammal is a human.

15. A method of inactivating $O^6$-alkylguanine-DNA-alkyltransferase (AGT) in a tumor cell comprising contacting said tumor cell with an effective amount of a compound or pharmaceutically acceptable salt of claim 1.

16. The compound or pharmaceutically acceptable salt of claim 2, wherein $R^1$ is hydrogen, halo, $C_1$-$C_4$ alkyl, $C_1$-$C_4$ hydroxyalkyl, mercapto, $C_1$-$C_4$ alkylthio, hydroxy, $C_1$-$C_4$ alkoxy, amino, $C_1$-$C_4$ aminoalkyl, $C_1$-$C_4$ alkylamino, $C_1$-$C_4$ dialkylamino, nitro, $C_1$-$C_4$ haloalkyl, $C_1$-$C_4$ cyanoalkyl, cyano, phenyl, phenylcarbonyl, or $C_1$-$C_4$ alkoxymethyl.

17. The compound or pharmaceutically acceptable salt of claim 2, wherein $R^2$ is hydrogen, halo, hydroxy, a $C_1$-$C_6$ alkyl, aryl, nitro, a $C_1$-$C_6$ hydroxyalkyl, a $C_1$-$C_8$ alkoxy, a aryloxy, amino, a $C_1$-$C_6$ alkylamino, a $C_1$-$C_6$ dialkylamino, carboxy, a carboxy-$C_1$-$C_6$ alkyl, cyano, a $C_1$-$C_6$ cyanoalkyl, or a $C_1$-$C_6$ aminoalkyl.

18. The compound or pharmaceutically acceptable salt of claim 2, wherein $X^2$ is hydrogen, halo, hydroxy, a $C_1$-$C_6$ alkyl, aryl, nitro, a $C_1$-$C_6$ hydroxyalkyl, a $C_1$-$C_8$ alkoxy, a aryloxy, amino, a $C_1$-$C_6$ alkylamino, a $C_1$-$C_6$ dialkylamino, carboxy, a carboxy-$C_1$-$C_6$ alkyl, cyano, a $C_1$-$C_6$ cyanoalkyl, or a $C_1$-$C_6$ aminoalkyl.

19. The compound or pharmaceutically acceptable salt of claim 3, wherein $X^1$ is selected from the group consisting of hydrogen, $C_1$-$C_6$ alkyl, $C_1$-$C_6$ aminoalkyl, $C_1$-$C_6$ hydroxyalkyl, $C_1$-$C_6$ alkylaminoalkyl, $C_1$-$C_6$ dialkylaminoalkyl, and $C_1$-$C_6$ cyanoalkyl.

20. A pharmaceutical composition comprising (a) a compound or pharmaceutically acceptable salt of claim 2 and (b) a pharmaceutically acceptable carrier.

21. A method of enhancing the chemotherapeutic treatment of tumor cells in a mammal with an antineoplastic alkylating agent that causes cytotoxic lesions at the $O^6$-position of guanine, which method comprises administering to the mammal an effective amount of the compound or pharmaceutically acceptable salt of claim 2, and administering to the mammal an effective amount of an antineoplastic alkylating agent which causes cytotoxic lesions at the $O^6$-position of guanine.

* * * * *